(12) United States Patent
Wallace et al.

(10) Patent No.: US 11,253,291 B2
(45) Date of Patent: Feb. 22, 2022

(54) LASER SLOTTED GRABBING DEVICE

(71) Applicant: STRYKER CORPORATION, Fremont, CA (US)

(72) Inventors: Michael P. Wallace, Pleasanton, CA (US); E. Skott Greenhalgh, Gladwyne, PA (US)

(73) Assignee: Stryker Corporation, Fremont, CA (US)

( * ) Notice: Subject to any disclaimer, the term of this patent is extended or adjusted under 35 U.S.C. 154(b) by 120 days.

(21) Appl. No.: 16/566,393

(22) Filed: Sep. 10, 2019

(65) Prior Publication Data

US 2020/0078045 A1 Mar. 12, 2020

Related U.S. Application Data

(60) Provisional application No. 62/729,311, filed on Sep. 10, 2018.

(51) Int. Cl.
*A61B 17/3207* (2006.01)
*A61B 17/22* (2006.01)
*A61B 17/00* (2006.01)

(52) U.S. Cl.
CPC ...... *A61B 17/320758* (2013.01); *A61B 17/22* (2013.01); *A61B 2017/00778* (2013.01); *A61B 2017/320733* (2013.01)

(58) Field of Classification Search
CPC . A61B 17/22; A61B 17/221; A61B 17/22031; A61B 17/32075; A61B 17/320725; A61B 17/320758
See application file for complete search history.

(56) References Cited

U.S. PATENT DOCUMENTS

| | | |
|---|---|---|
| 3,515,137 A | 6/1970 | Santomieri |
| 4,222,380 A | 9/1980 | Terayama |
| 4,243,040 A | 1/1981 | Beecher |
| 4,324,262 A | 4/1982 | Hall |
| 4,469,100 A | 9/1984 | Hardwick |
| 4,604,094 A | 8/1986 | Shook |

(Continued)

FOREIGN PATENT DOCUMENTS

| | | |
|---|---|---|
| AU | 2015210338 | 8/2015 |
| CN | 102186427 | 9/2011 |

(Continued)

OTHER PUBLICATIONS

Non-Final Office Action for U.S. Appl. No. 15/496,570, dated Aug. 9, 2017.

(Continued)

*Primary Examiner* — Tuan V Nguyen
(74) *Attorney, Agent, or Firm* — Vista IP Law Group, LLP

(57) ABSTRACT

Mechanical atherectomy and/or thrombectomy devices configured to remove obstructions (e.g., plaque material) of different consistencies and/or sizes from blood vessels. The devices may include a tractor comprising a flexible tube of material that inverts as it rolls over itself while being drawn into the open distal end of a catheter in a conveyor-like motion. The flexible tube can include features that facilitate engagement with the obstruction, enhance smooth tractor motion and/or promote movement control of the device within the blood vessel.

28 Claims, 23 Drawing Sheets

(56) References Cited

U.S. PATENT DOCUMENTS

| | | |
|---|---|---|
| 4,646,736 A | 3/1987 | Auth |
| 4,863,440 A | 9/1989 | Chin |
| 4,946,440 A | 8/1990 | Hall |
| 5,329,923 A | 7/1994 | Lundquist |
| 5,364,345 A | 11/1994 | Lowery et al. |
| 5,389,100 A | 2/1995 | Bacich et al. |
| 5,662,703 A | 9/1997 | Yurek et al. |
| 5,971,938 A | 10/1999 | Hart et al. |
| 6,156,055 A | 12/2000 | Ravenscroft |
| 6,221,006 B1 | 4/2001 | Dubrul et al. |
| 6,238,412 B1 | 5/2001 | Dubrul et al. |
| 6,245,078 B1 | 6/2001 | Ouchi |
| 6,258,115 B1 | 7/2001 | Dubrul |
| 6,544,278 B1 | 4/2003 | Vrba et al. |
| 6,569,181 B1 | 5/2003 | Burns |
| 6,620,179 B2 | 9/2003 | Brook et al. |
| 6,635,068 B1 | 10/2003 | Dubrul et al. |
| 6,635,070 B2 | 10/2003 | Leeflang et al. |
| 6,830,561 B2 | 12/2004 | Jansen et al. |
| 6,846,029 B1 | 1/2005 | Ragner et al. |
| 6,942,682 B2 | 9/2005 | Vrba et al. |
| 7,621,870 B2 | 11/2009 | Berrada et al. |
| 7,780,696 B2 | 8/2010 | Daniel et al. |
| 8,057,496 B2 | 11/2011 | Fischer, Jr. |
| 8,070,769 B2 | 12/2011 | Broome |
| 8,092,486 B2 | 1/2012 | Berrada et al. |
| 8,657,867 B2 | 2/2014 | Dorn et al. |
| 8,721,714 B2 | 5/2014 | Kelley |
| 8,784,442 B2 | 7/2014 | Jones et al. |
| 8,795,305 B2 | 8/2014 | Martin et al. |
| 8,956,384 B2 | 2/2015 | Berrada et al. |
| 9,028,401 B1 | 5/2015 | Bacich et al. |
| 9,125,683 B2 | 9/2015 | Farhangnia et al. |
| 9,126,016 B2 | 9/2015 | Fulton |
| 9,155,552 B2 | 10/2015 | Ulm, III |
| 9,173,668 B2 | 11/2015 | Ulm, III |
| 9,186,487 B2 | 11/2015 | Dubrul et al. |
| 9,358,037 B2 | 1/2016 | Farhangnia et al. |
| 9,259,237 B2 | 2/2016 | Quick et al. |
| 9,351,747 B2 | 5/2016 | Kugler et al. |
| 9,463,035 B1 | 10/2016 | Greenhalgh et al. |
| 9,643,035 B2 | 5/2017 | Mastenbroek |
| 9,717,514 B2 | 8/2017 | Martin et al. |
| 9,848,975 B2 | 12/2017 | Hauser |
| 9,849,014 B2 | 12/2017 | Kusleika |
| 9,962,178 B2 | 5/2018 | Greenhalgh et al. |
| 10,010,335 B2 | 7/2018 | Greenhalgh et al. |
| 10,016,266 B2 | 7/2018 | Hauser |
| 10,028,759 B2 | 7/2018 | Wallace et al. |
| 10,130,385 B2 | 11/2018 | Farhangnia et al. |
| 10,271,864 B2 | 4/2019 | Greenhalgh et al. |
| 10,327,883 B2 | 6/2019 | Yachia |
| 2002/0032455 A1 | 3/2002 | Boock et al. |
| 2002/0173819 A1 | 11/2002 | Leeflang et al. |
| 2003/0083693 A1 | 5/2003 | Daniel et al. |
| 2003/0135258 A1 | 7/2003 | Andreas et al. |
| 2003/0153873 A1 | 8/2003 | Luther et al. |
| 2003/0168068 A1 | 9/2003 | Poole et al. |
| 2003/0176884 A1 | 9/2003 | Berrada et al. |
| 2003/0208224 A1 | 11/2003 | Broome |
| 2004/0098033 A1 | 5/2004 | Leeflang et al. |
| 2004/0199202 A1 | 10/2004 | Dubrul et al. |
| 2005/0085826 A1 | 4/2005 | Nair et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1* | 8/2005 | Nguyen .............. A61F 2/01 606/159 |
| 2005/0283166 A1 | 12/2005 | Greenhalgh |
| 2005/0283186 A1 | 12/2005 | Berrada et al. |
| 2006/0042786 A1 | 3/2006 | West |
| 2006/0089533 A1 | 4/2006 | Ziegler et al. |
| 2006/0100662 A1 | 5/2006 | Daniel et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0276874 A1 | 12/2006 | Wilson et al. |
| 2006/0293696 A1 | 12/2006 | Fahey et al. |
| 2007/0112374 A1 | 5/2007 | Paul, Jr. et al. |
| 2007/0123798 A1 | 5/2007 | Rahamimov |
| 2007/0149996 A1 | 6/2007 | Coughlin |
| 2007/0213765 A1 | 9/2007 | Adams et al. |
| 2008/0183136 A1 | 7/2008 | Lenker et al. |
| 2009/0076417 A1 | 3/2009 | Jones |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0137846 A1 | 6/2010 | Desaietal |
| 2010/0190156 A1 | 7/2010 | Van Wordragen et al. |
| 2010/0249815 A1 | 9/2010 | Jantzen et al. |
| 2011/0034987 A1 | 2/2011 | Kennedy |
| 2011/0118817 A1 | 5/2011 | Gunderson et al. |
| 2011/0160763 A1 | 6/2011 | Ferrera et al. |
| 2011/0265681 A1 | 11/2011 | Allen et al. |
| 2011/0288529 A1 | 11/2011 | Fulton |
| 2011/0288572 A1 | 11/2011 | Martin |
| 2012/0059309 A1 | 3/2012 | Di Palma et al. |
| 2012/0083824 A1 | 4/2012 | Berrada et al. |
| 2012/0083868 A1 | 4/2012 | Shrivastava |
| 2012/0271105 A1 | 10/2012 | Nakamura et al. |
| 2013/0046332 A1 | 2/2013 | Jones et al. |
| 2013/0096571 A1 | 4/2013 | Massicotte et al. |
| 2013/0116721 A1 | 5/2013 | Takagi et al. |
| 2013/0226196 A1 | 8/2013 | Smith |
| 2013/0317589 A1 | 11/2013 | Martin et al. |
| 2013/0345739 A1 | 12/2013 | Brady et al. |
| 2014/0005712 A1 | 1/2014 | Martin et al. |
| 2014/0005717 A1 | 1/2014 | Martin et al. |
| 2014/0046133 A1 | 2/2014 | Nakamura et al. |
| 2014/0155980 A1 | 6/2014 | Turjman |
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0343593 A1 | 11/2014 | Chin et al. |
| 2014/0364896 A1* | 12/2014 | Consigny ............ A61B 17/221 606/200 |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick et al. |
| 2015/0088190 A1 | 3/2015 | Jensen |
| 2015/0164523 A1 | 6/2015 | Brady et al. |
| 2015/0164666 A1 | 6/2015 | Johnson et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0351775 A1 | 12/2015 | Fulton, III |
| 2016/0022293 A1 | 1/2016 | Dubrul et al. |
| 2016/0058540 A1 | 3/2016 | Don Michael |
| 2016/0074627 A1 | 3/2016 | Cottone |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0228134 A1 | 8/2016 | Martin et al. |
| 2017/0042571 A1 | 2/2017 | Levi |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0112513 A1 | 4/2017 | Marchand et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0348014 A1 | 12/2017 | Wallace et al. |
| 2018/0042624 A1 | 2/2018 | Greenhalgh et al. |
| 2018/0042626 A1 | 2/2018 | Greenhalgh et al. |
| 2018/0070968 A1 | 3/2018 | Wallace et al. |
| 2018/0236205 A1 | 8/2018 | Krautkremer et al. |
| 2019/0046219 A1 | 2/2019 | Marchand et al. |
| 2019/0117244 A1 | 4/2019 | Wallace et al. |

(56) References Cited

U.S. PATENT DOCUMENTS

| | | | |
|---|---|---|---|
| 2019/0133622 | A1 | 5/2019 | Wallace et al. |
| 2019/0133623 | A1 | 5/2019 | Wallace et al. |
| 2019/0133624 | A1 | 5/2019 | Wallace et al. |
| 2019/0133625 | A1 | 5/2019 | Wallace et al. |
| 2019/0133626 | A1 | 5/2019 | Wallace et al. |
| 2019/0133627 | A1 | 5/2019 | Wallace et al. |
| 2019/0336148 | A1 | 11/2019 | Greenhalgh et al. |

FOREIGN PATENT DOCUMENTS

| | | |
|---|---|---|
| CN | 103764049 | 4/2014 |
| CN | 104068910 | 10/2014 |
| CN | 104582608 | 4/2015 |
| CN | 108348319 | 7/2018 |
| CN | 111281482 | 6/2020 |
| EP | 1254634 | 11/2002 |
| GB | 1588072 | 4/1981 |
| GB | 2498349 | 7/2013 |
| WO | WO 00/32118 | 6/2000 |
| WO | WO 0202162 | 1/2002 |
| WO | WO 2009086482 | 7/2009 |
| WO | WO 2012009675 | 1/2012 |
| WO | WO 2012049652 | 4/2012 |
| WO | WO 2012162437 | 11/2012 |
| WO | WO 2015189354 | 12/2015 |
| WO | WO 2017058280 | 4/2017 |
| WO | WO 2017189535 | 11/2017 |
| WO | WO 2017189550 | 11/2017 |
| WO | WO 2017189591 | 11/2017 |
| WO | WO 2017189615 | 11/2017 |
| WO | WO 2017210487 | 12/2017 |
| WO | WO 2018049317 | 3/2018 |
| WO | WO 2019010318 | 1/2019 |
| WO | WO 2019094456 | 5/2019 |
| WO | WO 2019222117 | 11/2019 |

OTHER PUBLICATIONS

PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
PCT Invitation to Pay Additional Fees for International Appln. No. PCT/US2017/029345, Applicant Stryker Corporation, dated Oct. 17, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.
Non-final office action dated Feb. 1, 2018 for U.S. Appl. No. 15/496,668.
Response to Restriction for U.S. Appl. No. 15/496,668, filed Feb. 21, 2018.
International search report and written opinion dated Feb. 28, 2018 for PCT/US2017/029345, Applicant Stryker Corporation 26 pages.
Notice of Allowance dated Mar. 22, 2018 for U.S. Appl. No. 15/496,668.
Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
Invitation to Pay Additional Fees for International Patent Appln. No. PCT/US2018/059607 dated Jan. 31, 2019.
Japanese Office action dated Mar. 19, 2019 for Japanese Application No. 2018-535810 (with English Language translation).
International Search Report and Written Opinion dated Mar. 28, 2019 for International Appln. No. PCT/US2018/059607.
Notice of Allowance dated Apr. 10, 2019 for U.S. Appl. No. 15/611,546.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161(1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Restriction Requirement dated Apr. 11, 2019 for U.S. Appl. No. 15/497,092.
Response to Restriction Requirement filed Jun. 11, 2019 for U.S. Appl. No. 15/497,092.
Ex Parte Quayle office action dated Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).

(56) References Cited

OTHER PUBLICATIONS

Response to Restriction Requirement filed Jul. 25, 2019 for U.S. Appl. No. 15/700,685.
Response to Ex Parte Quayle office action filed Jul. 25, 2019 for U.S. Appl. No. 15/497,092.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 2 pgs.; retrieved/printed: Mar. 24, 2016.
YouTube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
Notice of Allowance for U.S. Appl. No. 15/043,996 dated Jun. 9, 2016.
Ex Parte Quayle office action dated Aug. 2, 2019 for U.S. Appl. No. 15/497,092.
Non Final Office Action dated Aug. 23, 2019 for U.S. Appl. No. 15/700,685.
Non Final Office Action dated Sep. 3, 2019 for U.S. Appl. No. 15/794,939.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Amendment Response to Non-Final Office Action for U.S. Appl. No. 16/183,171 dated Jul. 30, 2020.
Amendment Response to Non-Final Office Action for U.S. Appl. No. 16/183,162 dated Jul. 30, 2020.
Applicant Interview Summary for U.S. Appl. No. 16/096,031 dated Jul. 30, 2020.
Applicant Interview Summary for U.S. Appl. No. 16/169,334 dated Jul. 30, 2020.
Applicant Interview Summary for U.S. Appl. No. 16/183,133 dated Aug. 24, 2020.
Non-Final Office Action for U.S. Appl. No. 16/183,149 dated Aug. 18, 2020.
Extended European Search Report for EP Patent Appln. No. 20185092.2 dated Sep. 11, 2020.
EP Examination Report for EP Patent Appln. No. 18745794.0 dated Jul. 20, 2020.
Amendment Response to NFOA for U.S. Appl. No. 16/183,149 dated Sep. 25, 2020.
PCT International Preliminary Report on Patentability for International Appln. No. PCT/US2019/050410 dated Mar. 25, 2021.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.
Notice of Allowance dated Oct. 24, 2019 for U.S. Appl. No. 15/611,546.
Response to Non Final Office Action filed Nov. 8, 2019 for U.S. Appl. No. 15/700,685.
Notice of Allowance dated Nov. 6, 2019 for U.S. Appl. No. 15/795,097.
Rule 71(3) Allowance for EP Patent Appln. No. 17721036.6 dated Oct. 23, 2019.
Rule 71(3) Allowance for EP Patent Appln. No. 17722290.8 dated Nov. 11, 2019.
Notice of Allowance dated Nov. 21, 2019 for U.S. Appl. No. 15/700,685.
Amendment Response dated Dec. 3, 2019 for U.S. Appl. No. 15/794,939.
PCT International Search Report and Written Opinion for International Patent Appln. No. PCT/US2019/050467, Applicant Stryker Corporation, dated Dec. 18, 2019 (17 pages).
Non Final Office Action dated Dec. 27, 2019 for U.S. Appl. No. 16/594,256.
Final Office Action dated Mar. 2, 2020 for U.S. Appl. No. 15/794,939.
Notice of Allowance for U.S. Appl. No. 15/794,939 dated Mar. 31, 2020.
Amendment Response dated Mar. 27, 2020 for U.S. Appl. No. 16/594,256.
Non-Final Office Action for U.S. Appl. No. 16/096,031 dated May 8, 2020.
Non-Final Office Action for U.S. Appl. No. 16/183,162 dated May 13, 2020.
Non-Final Office Action for U.S. Appl. No. 16/169,334 dated May 8, 2020.
Non-Final Office Action for U.S. Appl. No. 16/183,171 dated May 13, 2020.
Foreign OA for Japanese Patent Application No. 2018-535810 dated Feb. 7, 2020.
Foreign OA for JP Patent Appln. No. 2019-507078 dated Feb. 3, 2021.
Foreign OA for JP Patent Appln. No. 2019-507075 dated Feb. 1, 2021.
Notice of Allowance for U.S. Appl. No. 16/397,089 dated Feb. 18, 2021.
Foreign OA for JP Patent Appln. No. 2018-562633 dated Mar. 4, 2021.
Notice of Allowance for U.S. Appl. No. 16/183,149, dated Oct. 9, 2020.
Foreign OA for CN Patent Appl. No. 2017800393642, dated Dec. 1, 2020.
Foreign OA for CN Patent Appl. No. 2017800393676, dated Dec. 2, 2020.
Foreign OA for CN Patent Appl. No. 2017800396566, dated Dec. 3, 2020.
Foreign OA for CN Patent Appl. No. 2017800343357, dated Jan. 6, 2021.

(56) References Cited

OTHER PUBLICATIONS

Applicant's Response filed in EP Patent Appl. No. 18807524.6, dated Dec. 21, 2020.
PCT International Search Report and Written Opinion for International Appl. No. PCT/US2020/014854, dated Oct. 5, 2020 (13 pages).
PCT International Search Report and Written Opinion for International Appl. No. PCT/US2020/018655, applicant Magic Leap, Inc., dated Dec. 16, 2020 (22 pages).
PCT International Search Report and Written Opinion for International Appl. No. PCT/US2020/017684, dated Nov. 30, 2020 (19 pages).
Foreign Notice of Reasons of Rejection for JP Patent Appln. No. 2019-513286 dated Jul. 26, 2021 (with English translation).
Foreign Exam Report for EP Patent Appln. No. 19773654.9 dated Aug. 24, 2021.
Foreign OA for JP Patent Appln. No. 2020-093260 dated Apr. 20, 2021.
Non-Final Office Action for U.S. Appl. No. 16/594,259 dated Aug. 31, 2021.
Foreign OA for CN Patent Appln. No. 201780067034.4 dated Sep. 3, 2021 (with English translation).
Foreign Search Report for CN Patent Appln. No. 201780067034.4 dated Aug. 30, 2021 (with English translation).
Response to OA for EP Patent Appln. No. 19773654.9 dated Dec. 22, 2021 with Amended Claims and Description.

* cited by examiner

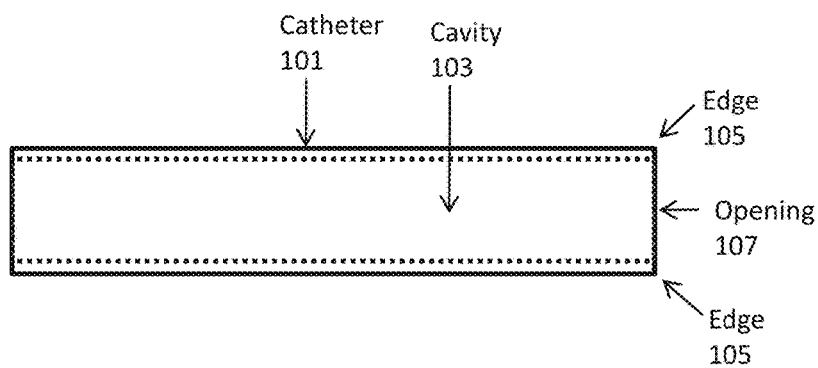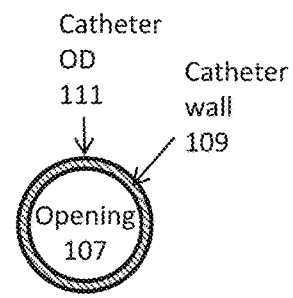
FIG. 1A  FIG. 1B
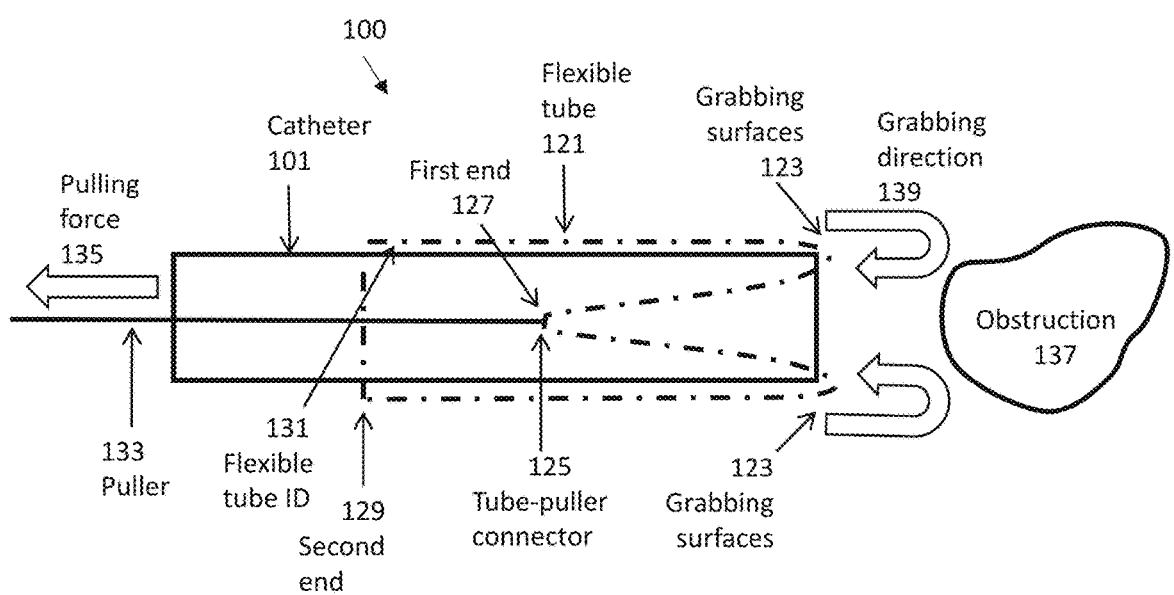
FIG. 2

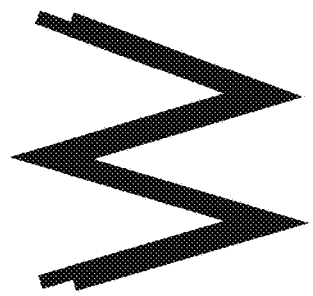
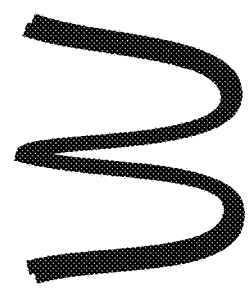
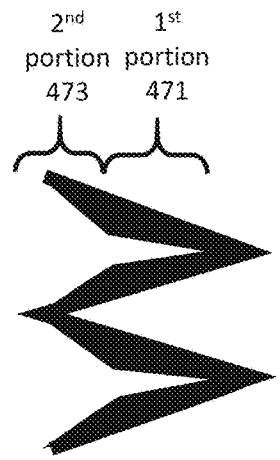
FIG. 4A  FIG. 4B  FIG. 4C
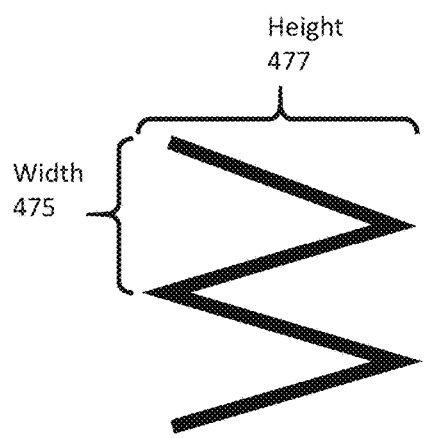
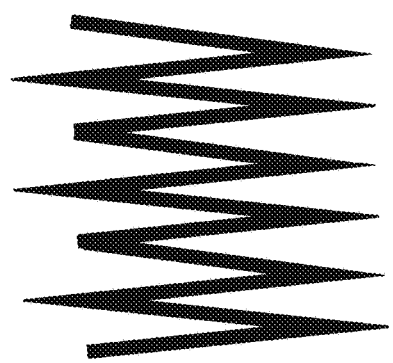
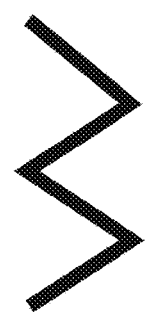
FIG. 4D  FIG. 4E  FIG. 4F
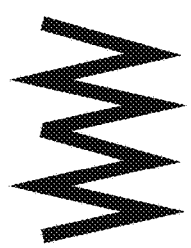
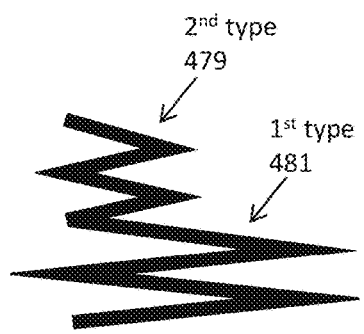
FIG. 4G  FIG. 4H  FIG. 4I

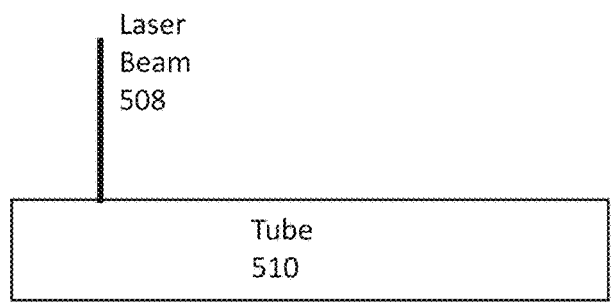
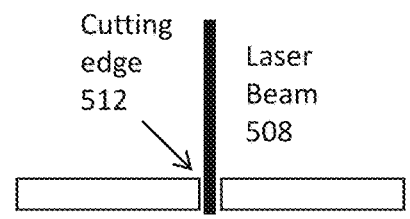
FIG. 5A  FIG. 5B
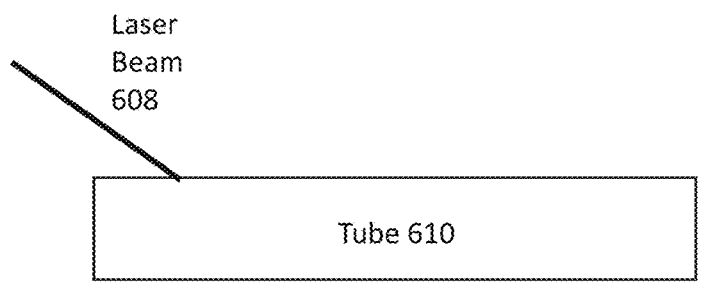
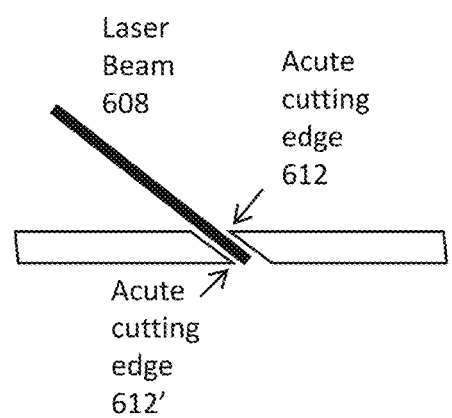
FIG. 6A  FIG. 6B

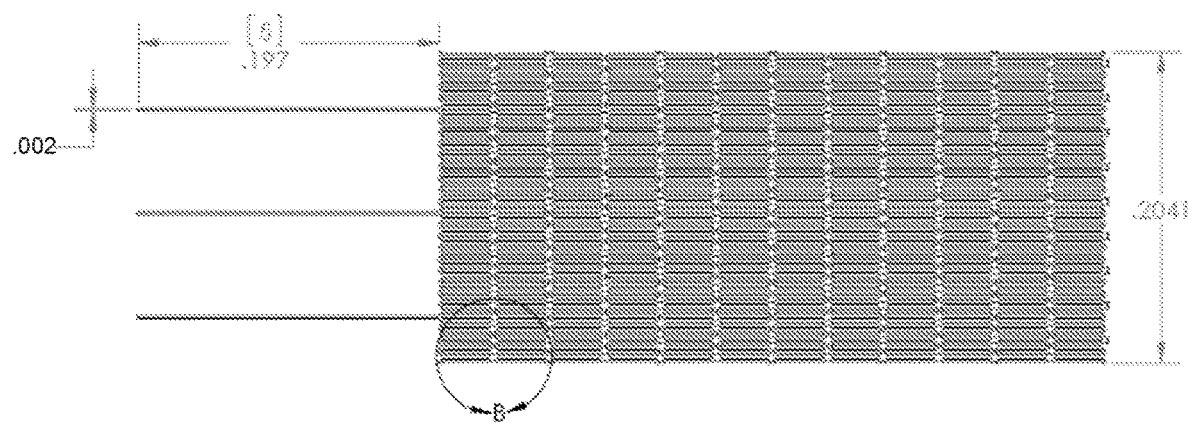
16A
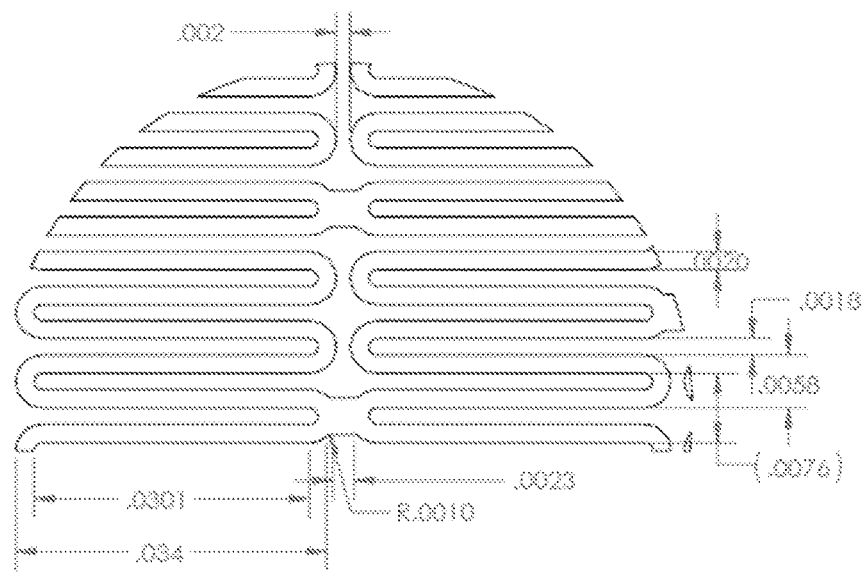
FIG. 16B

LASER SLOTTED GRABBING DEVICE

CROSS REFERENCE TO RELATED APPLICATIONS

This patent claims priority to U.S. provisional patent application No. 62/729,311, filed on Sep. 10, 2018, titled "Laser Slotted Grabbing Device," the entirety of which is herein incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices and methods described herein relate to mechanical removal of objects within a body. In particular, described herein are thrombectomy and atherectomy devices and methods.

BACKGROUND

Maintenance of blood fluidity within the vascular system is an important physiological process. Normally, blood flows freely through a blood vessel to carry blood with oxygen and nutrients to different tissues of the body. If the blood vessel is injured, the body's normal response is to form a clot that serves to limit blood hemorrhaging. This normal response is referred to as hemostasis. A thrombus is a blood clot that results when hemostasis is excessively activated in the absence of bleeding. A thrombus can stem from any of a number of causes, such as trauma, various conditions that cause abnormal blood flow or blood coagulation conditions. A thrombus in a large blood vessel may decrease blood flow through that vessel. In a small blood vessel, blood flow may be completely cut off, resulting in death of tissue supplied by that vessel.

A thrombectomy is a procedure for removing a blot clot from a vessel to restore blood flow within the vessel. Catheter-based thrombectomy techniques involve inserting a catheter through the blood vessel in order to reach the clot and remove it from the vessel. As with many medical procedures, it is desirable to reduce the occurrence of damage to the tissues and cells during a thrombectomy. For example, minimally invasive techniques may include limiting the size of any incisions associated with the procedure. For a thrombectomy, a minimally invasive procedure may involve inserting a smaller catheter within the blood vessel to lessen the amount of damage to the vessel and surrounding tissues. Although catheter-based thrombectomy technologies may incorporate minimally invasive techniques, challenges still remain. For example, the catheter device should be able to effectively and efficiently remove the blood clot from a blood vessel while maintaining a small profile in order to reduce damage to tissues. Therefore, there is a need for space efficient and effective grabbing devices for catheter-based procedures.

SUMMARY OF THE DISCLOSURE

The present disclosure relates to grabbing devices suitable for use in removing an obstruction from a blood vessel. The grabbing devices can include a catheter having an inner cavity and a flexible scraping tube (e.g., tractor) that is configured to engage with an obstruction within a blood vessel and to direct the obstruction toward the inner cavity of the catheter. The tractor may be reciprocated. Described herein are various configurations of the catheter, tractor and other features of the grabbing device that can facilitate the capture and removal of an obstruction from a blood vessel.

In some embodiments, the tractor comprises a flexible tube that includes a number of engagement features that are configured to engage with the obstruction. The engagement features are configured to scrape against, so as to remove (e.g., by cutting, taring, chipping, pulling, etc.) plaque from the vessel wall(s). The engagement features may be arranged on a series of bands that are held together by a number of band connectors. Features of the tractor, such as the material, wall thickness, number and size of bands, engagement feature shapes and sizes, and number and placement of band connectors can be configured to emphasize or optimize various functions of the grabbing device. The operation of the grabbing device may be evaluated based on a number of performance parameters, such as rolling force, grabbing strength, maneuverability (e.g., within the blood vessel), durability and radio-opacity.

As will be described in greater detail below, the tractor is generally configured to roll from outside of the catheter into the inner lumen of the catheter, everting over the distal end of the catheter so that the engagement features extending from the tractor (on all sides or just a sub-region, e.g., one side or region of the tractor) may scrape against and/or remove plaque material. The tractor may be continuously rolled (e.g., pulled into the catheter or out of the catheter, through preferably into) and/or may be reciprocated, e.g., rolled out of, then into, the catheter. In some variations the tractor is moved in a ratcheting manner, so that it is reciprocated, but with a net movement into the catheter, to drawn in material removed by the engagement features. For example, the tractor may be pulled or driven into the catheter distal end in a first distance, then withdrawn out of the catheter distal end in a second, opposite, direction, a second distance that is slightly less than the first distance, resulting in a net overall movement into the catheter.

By way of example and without limitation, in one exemplary embodiment of the disclosed inventions, an atherectomy device for removing a plaque material from a blood vessel includes a catheter having a distal edge defining an opening that provides access to a lumen within the catheter, and a tractor comprising a flexible tube that at least partially covers and extends along an outer surface of the catheter and inverts over the catheter distal edge, such that a first end of the flexible tube extends through the opening into the lumen of the catheter, wherein the flexible tube comprises a plurality of engagement features cut at an acute angle into an outer surface of the flexible tube to form a plurality of acute cutting edges, and wherein the flexible tube is configured so that pulling the first end of the flexible tube proximally through the catheter lumen causes the flexible tube to roll and invert over the catheter distal edge, thereby exposing the acute cutting edges distally as the flexible tube rolls into the catheter lumen.

The acute cutting edges may be circumferentially spaced apart or aligned, or some of each, along a length of the flexible tube, and may be configured to scrape or gouge the plaque material on a wall of the blood vessel when the first end of the flexible tube is pulled proximally through the catheter lumen. By way of example, the engagement features may be arranged into a series of circumferential bands spaced apart longitudinally along a length of the flexible tube, such that the respective bands of engagement features pass sequentially over the distal edge of the catheter as the flexible tube rolls into the catheter lumen. The atherectomy device may further include respective links that extend between adjacent bands of engagement features, wherein the links may be arranged in a circumferentially offset pattern, a circumferentially aligned pattern, or some of each, along the length of the flexible tube.

By way of further examples, and without limitation, the engagement features may include a first set of features defined by having a first aspect ratio, and a second set of features defined by having a second aspect ratio that is different than the first aspect ratio. For example, the engagement features may include a first set of features defined by having sharp engagement surfaces, and a second set of features defined by having curved engagement surfaces. Additionally, or alternatively, engagement features of a first set of the engagement features may have a first shape configured for shoveling the plaque material, and engagement features of a second set of the engagement features may have a second shape configured for gouging the plaque material. For example, in one embodiment, engagement features of a first set of the engagement features have a first shape configured for cutting the plaque material, and engagement features of a second set of the engagement features have a second shape configured for gouging the plaque material. In another embodiment, engagement features of a first set of the engagement features have a first shape configured for cutting the plaque material, engagement features of a second set of the engagement features have a second shape configured for gouging the plaque material, and engagement features of a third set of the engagement features have a third shape configured for shoveling the plaque material.

In another exemplary embodiment of the disclosed inventions, an atherectomy device for removing a plaque material from a blood vessel includes a catheter having distal end portion configured for entering the blood vessel, and a distal edge that defines an opening that provides access to an internal lumen of the catheter, and an activatable tractor comprising a flexible tube that at least partially covers and extends along an outer surface of the distal end portion of the catheter and inverts over the catheter distal edge, such that an end portion of the flexible tube extends through the opening into the internal lumen of the catheter, the flexible tube having an outer surface comprising engagement features having a plurality of different shapes, wherein when the tractor is activated, the flexible tube moves around the catheter distal edge such that the engagement features protrude from the distal edge to engage with and direct the plaque material toward the internal lumen. Without limitation, the tractor may be configured such that, when the tractor is activated, the flexible tube moves around the catheter distal edge in a reciprocating motion.

The engagement features may include a first set of protruding features defined by having a first aspect ratio and a second set of protruding features defined by having a second aspect ratio different than the first aspect ratio. For example, the engagement features may include a first set of protruding features defined by having sharp engagement surfaces and a second set of protruding features defined by having curved engagement surfaces.

Additionally, or alternatively, engagement features of a first set of the engagement features may have a first shape configured for shoveling the plaque material, and engagement features of a second set of the engagement features have a second shape configured for gouging the plaque material. For example, a first set of the engagement features may have a first shape configured for cutting the plaque material, and a second set of the engagement features may have a second shape configured for gouging the plaque material. In one embodiment, engagement features of a first set of the engagement features have a first shape configured for cutting the plaque material, engagement features of a second set of the engagement features have a second shape configured for gouging the plaque material, and engagement features of a third set of the engagement features have a third shape configured for shoveling the plaque material.

In yet another exemplary embodiment of the disclosed inventions, an atherectomy device for removing a plaque material from a blood vessel includes a catheter having a distal edge that defines an opening that provides access to an internal lumen; and an activatable tractor comprising a flexible tube that covers at least a portion of the distal edge and enters the catheter lumen, the flexible tube having an outer surface comprising a series of longitudinally spaced apart circumferential bands of engagement features configured to engage with the plaque material, wherein the engagement features of at least two adjacent bands are circumferentially offset from one another, and wherein, when the tractor is activated, the bands pass sequentially over the catheter distal edge such that the engagement features protrude from the distal edge to engage and direct the plaque material toward the catheter lumen.

Without limitation, each band may have three to five engagement features per centimeter length of the band, and the flexible tube may have two to three bands per centimeter length of the flexible tube. Links may be provided between respective adjacent bands of engagement features, wherein the links may be arranged in a circumferentially offset pattern, a circumferentially aligned pattern, or some of each pattern along the length of the flexible tube. The flexible tube may be provided with fastening elements that couple the flexible tube to a puller disposed in the catheter lumen.

Other and further aspects and features of the disclosed inventions are described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A and 1B show a side view and a cross section view, respectively, of a catheter.

FIG. 2 shows a side view of a catheter with a tractor having grabbing surfaces.

FIGS. 4A-4I show plan views of various cutting patterns for forming various engagement features of a tractor.

FIGS. 5A and 5B show different laser cutting operations for forming engagement feature of a tractor.

FIGS. 6A and 6B illustrate one method of forming an engagement feature of a tractor by cutting (e.g., in this example, using a laser) at an angle relative to the surface of the tractor, to form an acute cutting edge on one portion of the engagement feature. FIG. 6A shows a view of the overall flexible tube (e.g., a metal, such as Nitinol, or polymeric tube) while FIG. 6B shows an enlarged region.

FIG. 11B shows an enlarged view of section A of FIG. 11A.

FIG. 13B shows an enlarged view of section A of FIG. 13A; the dimensions shown in FIGS. 13A-13B are intended only as one example, actual dimensions may be different.

FIGS. 14A-14B shows an enlarged view of section B of FIG. 14A; the dimensions shown in FIG. 14B are intended only as one example, actual dimensions may be different.

FIG. 15B shows an enlarged view of section B of FIG. 15A; the dimensions shown in FIGS. 15A-15B are intended only as one example, actual dimensions may be different.

FIGS. 16A-16B show a plan views of a variation of a strut network having openings and struts that may form the tractor portion of a device (e.g., an atherectomy device) as described herein. FIG. 16B shows an enlarged view of section B of FIG. 16A; the dimensions shown in FIGS. 16A-16B are intended only as one example, actual dimensions may be different.

FIG. 17B shows an enlarged view of section B of FIG. 17A; the dimensions shown in FIGS. 17A-17B are intended only as one example, actual dimensions may be different.

FIG. 18B shows an enlarged view of section B of FIG. 18A; the dimensions shown in FIGS. 18A-18B are intended only as one example, actual dimensions may be different.

FIG. 19B shows an enlarged view of section B of FIG. 19A; the dimensions shown in FIGS. 19A-19B are intended only as one example, actual dimensions may be different.

FIG. 20B shows an enlarged view of section B of FIG. 20A; the dimensions shown in FIGS. 20A-20B are intended only as one example, actual dimensions may be different.

FIG. 21B shows an enlarged view of section B of FIG. 21A; the dimensions shown in FIGS. 21A-21B are intended only as one example, actual dimensions may be different.

FIG. 22B shows an enlarged view of section B of FIG. 22A; the dimensions shown in FIGS. 22A-22B are intended only as one example, actual dimensions may be different.

FIG. 23B shows an enlarged view of section B of FIG. 23A; the dimensions shown in FIGS. 23A-23B are intended only as one example, actual dimensions may be different.

FIG. 24B shows an enlarged view of section B of FIG. 24A; the dimensions shown in FIGS. 24A-24B are intended only as one example, actual dimensions may be different.

DETAILED DESCRIPTION

Figure 3A:
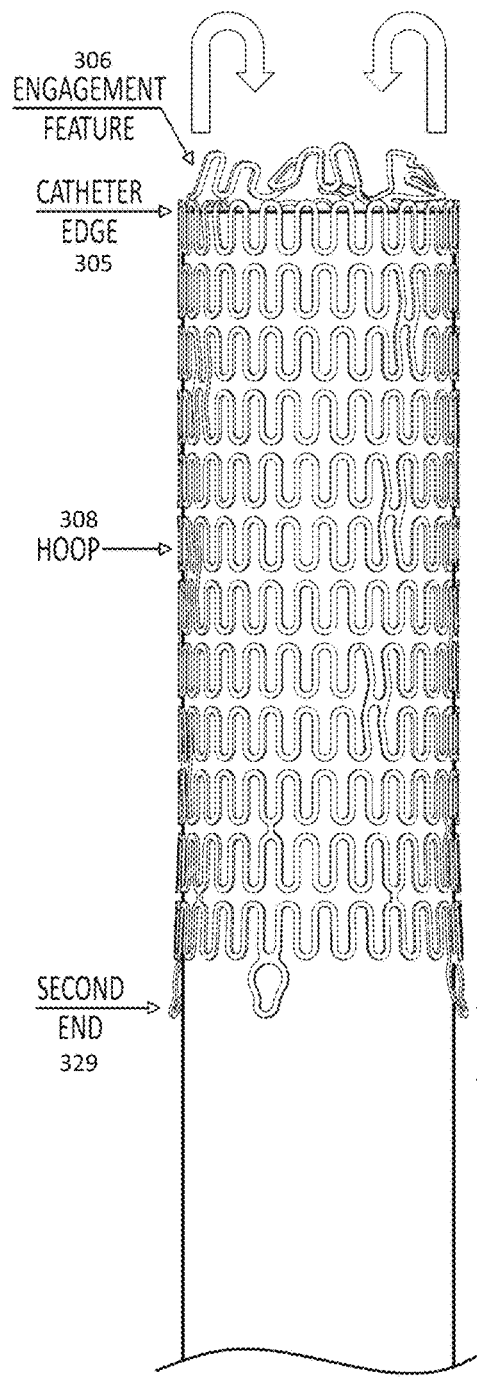
FIGS. 3A and 3B show perspective views of tractors indicating various tractor features.

Described herein are catheter-based grabbing devices for removing obstructions from a blood vessel. The devices may be suitable for use in a thrombectomy and/or an atherectomy (e.g., a plaque removal). A thrombectomy is a procedure for removing a blood clot, also referred to as a thrombus, from a blood vessels. A blood clot can contain a combination of blood components such as platelets and red blood cells. An atherectomy is a procedure for removing an atheroma, also referred to as an atheromatous plaque (or simply plaque), from a blood vessel. An atheroma can contain an accumulation of degenerative material, which may include macrophage cells, or debris, containing lipids, calcium and a variable amount of fibrous connective tissue.

The properties of blood vessel obstructions can vary greatly. For example, some blood clots can have a soft jelly-like consistency. More mature blood clots may have a firmer consistency, similar to that of gummy bear candy. An atheroma may have a more firm consistency, such as similar to that of wax, lipstick or even as hard as hard candy. Some obstructions can be very large, especially in peripheral regions such as the legs. In some cases, the obstructions can be as long as tens of centimeters (e.g., 30 cm) in length. Other obstructions can be much smaller but may still obstruct the flow of blood if they reside within smaller blood vessels.

The grabbing devices described herein can be configured to capture and remove blood vessel obstructions and/or plaques having a wide range of sizes and consistencies. The grabbing devices may include a tractor comprising a flexible tube of material that inverts as it rolls over itself while being drawn into a catheter in a conveyor-like motion. The flexible tube can have engagement feature that are configured to protrude from a distal end of the catheter in a rotating motion. The protruding engagement features can engage with the obstruction and pull at least a portion of the obstruction into the catheter. In some cases, the grabbing devices are configured to capture the obstruction in whole. In some cases, the grabbing devices are configured to break up the obstruction to more manageably-sized pieces before or during the capturing process. The shapes, sizes and rigidity of the engagement features can be selected so as to increase the capture efficiency of the grabbing device, which can be based at least in part on properties of the obstruction.

The grabbing device (e.g., atherectomy device) can include a number of grabbing surfaces, which are supported by a support structure. In some embodiments, the support structure includes a catheter. FIGS. 1A and 1B show a side view and a cross section view, respectively, of a catheter 101 in accordance with some embodiments. At least a portion of the catheter may be a tube having an outer surface 109, inner surface, and an edge 105 (also referred to as a rim) that at least partially defines an opening. The opening can have any shape and size. For example, the opening can have a round, oval or elliptical shape. The length and diameter (outer diameter and/or inner diameter) of the catheter can vary, depending on application requirement. For example, a catheter having a smaller outer diameter (catheter OD 111) may be suitable for inserting with smaller blood vessels, a catheter having a larger outer diameter may be suitable for inserting with larger blood vessels. The opening of the catheter can provide access to an internal cavity within the catheter.

The grabbing device 100 can include a flexible material (e.g., tractor tube), which can be configured to wrap around at least a portion of the outer surface, and at least partially enter the internal cavity of the catheter. In some cases, the flexible material is configured to form a tube shape. FIG. 2 shows a side view of a catheter 101 with a flexible tube 121, which can be part of a tractor configured to pull an obstruction. The flexible tube can have an inner diameter (flexible tube ID) in associated with the outer diameter of the catheter. In some cases, the flexible tube directly contacts the outer surface of the catheter. In some cases, one or more intermediate layers (e.g., sleeves, not shown) is/are between the flexible tube and the outer surface of the catheter. In some cases, the outer surface of the catheter and/or an inner surface of the flexible tube has a coating (e.g., low friction coating). The coating may include a hydrophilic coating or a lubricant. In some embodiments, the outer surface of the catheter and/or an inner surface of the flexible tube has a smoothed (e.g., polished) surface. For example, a laser polishing process may be used to smooth portions of the flexible tube.

The flexible tube may be any appropriate length. For example, the flexible tube may be between 3 to 100 centimeters (cm) long (e.g., between 3 and 50 cm, between 3 and 40 cm, between 3 and 30 cm, between 3 and 20 cm, between 10 and 100 cm, between 10 and 50 cm, between 20 and 100 cm, between 20 and 50 cm, etc.).

The flexible tube can have a first end 127, which can be operationally coupled with one or more pulling devices to place a pulling force on the flexible tube. Pulling device (puller 133) can be a wire, rod, catheter, tube, etc.). The pulling force 135 can cause the flexible tube to retract into the internal cavity of the catheter, thereby inverting at least a portion of the flexible tube. In some cases, the pulling force includes a vacuum force and/or one or more mechanical pullers. In some embodiments, the puller(s) includes one or more wires, catheters and/or strings. The puller(s) may be positioned within the catheter and/or outside of the catheter. The puller(s) may be operationally coupled with one or more actuators and/or motors that drive the pulling force. In some variations a second puller (not shown) may be attached to the second end 129 to allow the flexible tube to be reciprocated over (in/out) of the distal end of the catheter. The second puller may be one or more wires, a tube or sleeve, etc. The amount of force may vary depending on the application. In some cases, the one or more actuators and/or motors is configured to apply less than 300 grams (g) of force (e.g., less than 400 g, less than 300 g of force, less than 200 g of force, less than 100 g of force, less than 90 g of force, less than 80 g of force, less than 70 g of force, less than 60 g of force, less than 50 g of force, less than 10 g of force, etc.) to the first end of the flexible tube. The force required to retract the flexible tube into the catheter typically refers to the force required to roll the flexible tube over the distal end of the catheter; an initial deployment force (e.g., to release the end of the tractor outside of the catheter) may be greater than the force required to retract the catheter (e.g., greater than 100 g of force, 200 g of force, 300 g of force, 400 g of force, 500 g of force, 600 g of force, 700 g of force, 800 g of force, 900 g of force, 1000 g of force, 1500 g of force, 2000 g of force, etc.).

During operation, a pulling force 135 applied to the first end 127 of the flexible tube can cause the flexible tube to pass over the distal end edge of the catheter such that grabbing surfaces extending from the distal end edge of the catheter in a grabbing direction. When the flexible tube comes in contact with an obstruction, the grabbing surfaces 123 can engage with and pull the obstruction toward the internal cavity. In some variations, the puller may push or push and pull, e.g., when reciprocating the tractor. Thus, the flexible tube can act as a tractor that cooperates with the catheter to apply a drawing force on the obstruction. Once at least a portion of the obstruction is sufficiently secured by the grabbing device, the grabbing device can be removed from the blood vessel with the obstruction secured within the cavity, thereby removing the obstruction from the blood vessel. Once removed from the blood vessel, in some embodiments the grabbing device is configured to release the obstruction material 137 from within the internal cavity by reversing the direction of the tractor (e.g., in the grabbing direction 139). For example, a pulling force can be applied to the second end of the flexible tube, thereby causing the flexible tube to roll over the edge of the catheter in a releasing direction that is opposite the grabbing direction.

In some applications, the grabbing device is guided within a least a portion of the blood vessel using a guide catheter. For example, the grabbing device can be inserted co-axially through an internal cavity of the guide catheter. In such cases, the grabbing device can be configured to track/slide within the guide catheter with minimal friction. For example, an outer surface of the flexible tube (e.g., in contact with the inner surface of the guide catheter) can include one or more low friction coatings (e.g., hydrophilic coating and/or lubricant). In some cases, one or more intermediate layers (e.g., sleeves) is placed between the outer surface of the flexible tube and the inner surface of the guide catheter. In some embodiments, the outer surface of the flexible tube has a smoothed (e.g., polished) surface. Such low friction features can allow the grabbing device to be moved forward, backward and/or axially rotated (twisted) with little force.

Figure 3B:
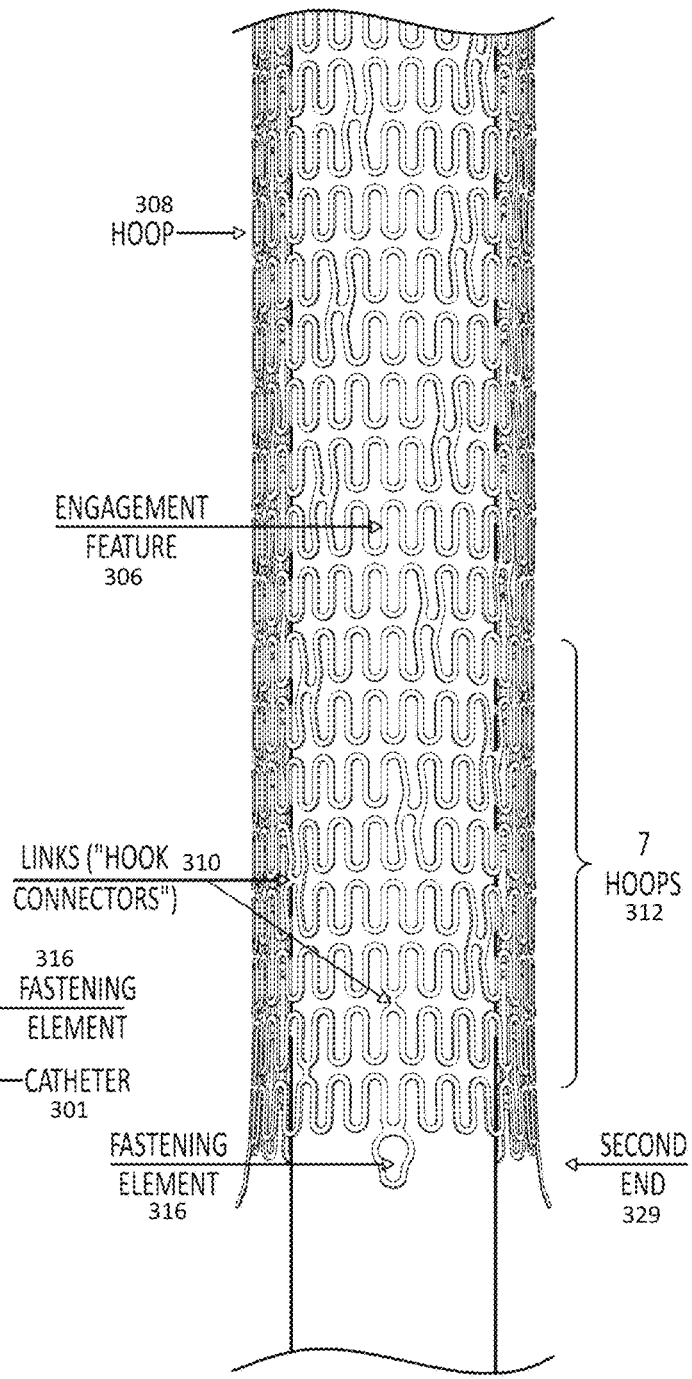

The grabbing features of the flexible tube can be configured to engage with the obstruction in a manner that facilitates capture of the obstruction within the grabbing device. FIGS. 3A and 3B show perspective views of different flexible tubes, in accordance with some embodiments. The grabbing features 306 can include a series of bands (also referred to as hoops 308 or rows), which are connected to each other via connectors 310 (also referred to as band connectors, hoop connectors or row connectors or links). The hoops can include multiple engagement features that are configured to engage with the obstruction. FIG. 3B shows a portion of a flexible tube having seven (7) consecutive hoops per centimeter 312 and twenty (20) engagement features 306 per hoop perimeter. At least some of the engagement features within a given hoop can be configured to project from the distal end of the catheter 301 as the hoop rolls over the edge 305 of the catheter. The first end and/or the second end 329 of the flexible tube may include one or more fastening elements 316 that are configured to facilitate the coupling of the flexible tube with one or more pull and/or push connectors (e.g., wires, strings, tubes, etc.). The fastening elements may correspond to fingers that extend from the flexible tube (e.g., from one of hoops), and that include one or more openings configured to accept the pull and/or push connector (s).

The flexible tube may be formed of any type of material, such as fibrous material (e.g., natural and/or synthetic), polymer material and/or metal material. Metal materials can include metal alloys and/or pure metal material. In some cases, the type of material may be chosen based on its rigidity or malleability. The various engagement features, hoops, hoop connectors and/or fastening elements can be formed using any process. In some embodiments, a laser cutting process is used, which may provide precision cutting of small dimensions. The laser cutting process may involve directing a laser beam at a sheet or tube of material (e.g., metal or plastic) to cut a pattern of openings (e.g., holes and/or slits) within the sheet or tube. The material between the openings form a network of struts, where at least some of the struts correspond to the engagement features of the tractor. If the material is in the form of sheet, the sheet may be rolled into a tubular form with the ends of the sheet coupled using any technique (e.g., welding, melting, gluing, etc.).

Figure 10:
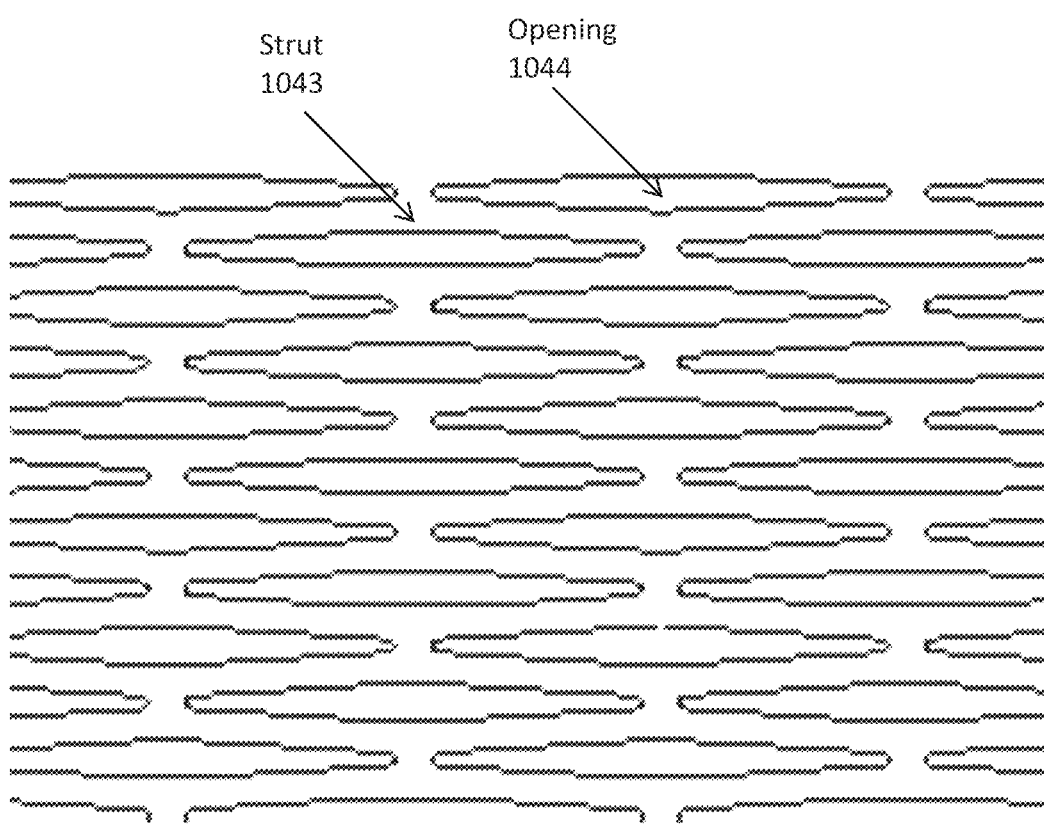
FIG. 10 shows a plan view of a cut pattern for a tractor with multiple openings and a network of struts.
Figure 11A:
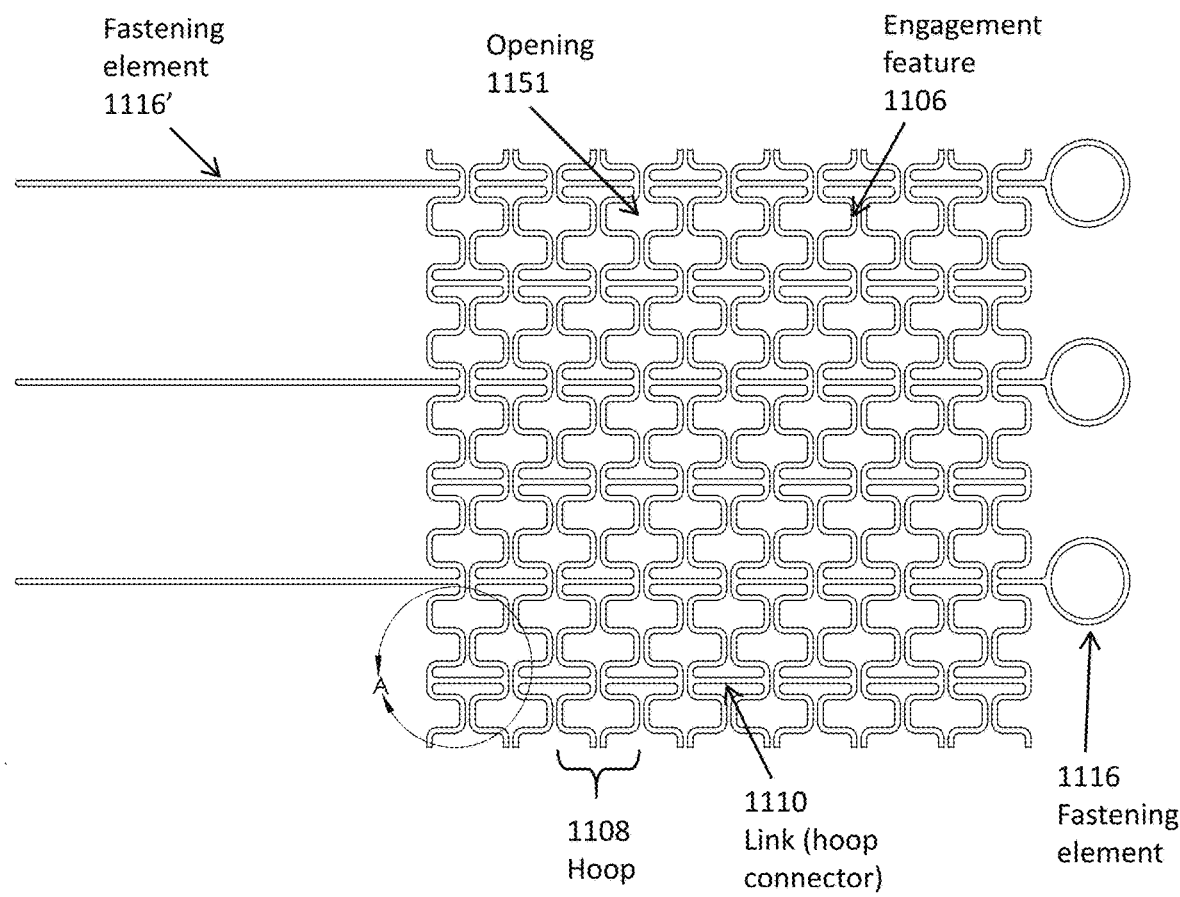
FIGS. 11A-11B show a plan views of one variation of a strut network having openings and struts that may form the tractor portion of a device (e.g., an atherectomy device) as described herein.
Figure 11B:
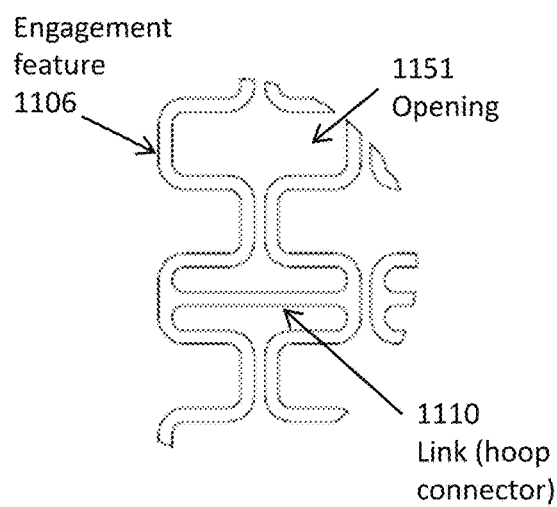
Figure 12:
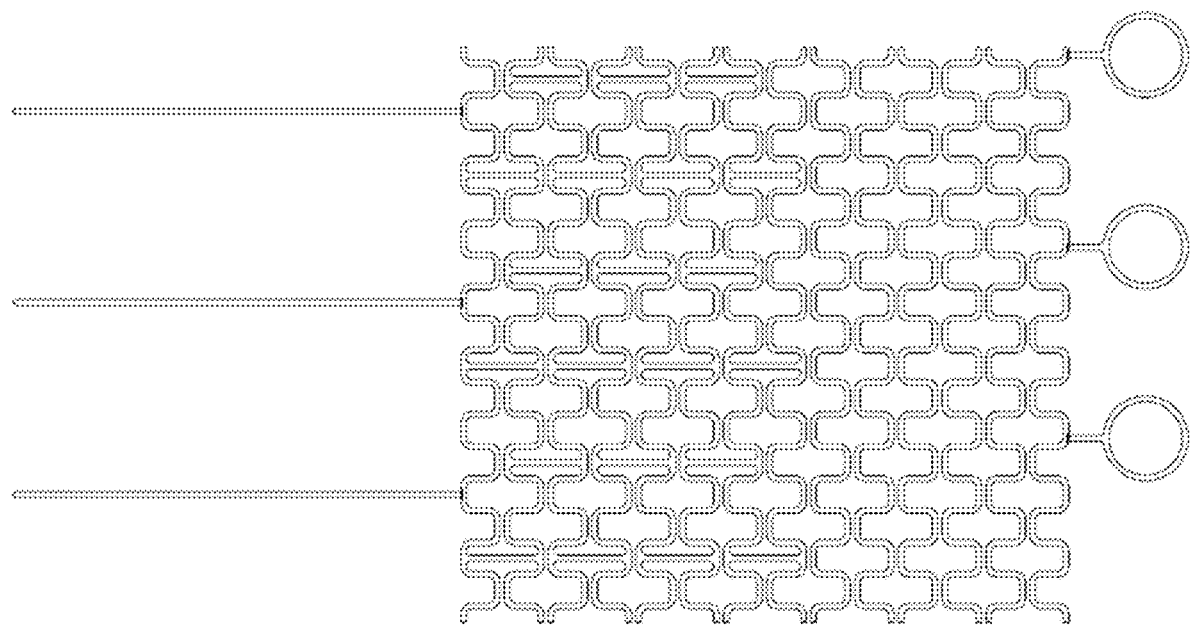
FIG. 12 shows a plan views of one variation of a strut network having openings and struts that may form the tractor portion of a device (e.g., an atherectomy device) as described herein.
Figure 13A:
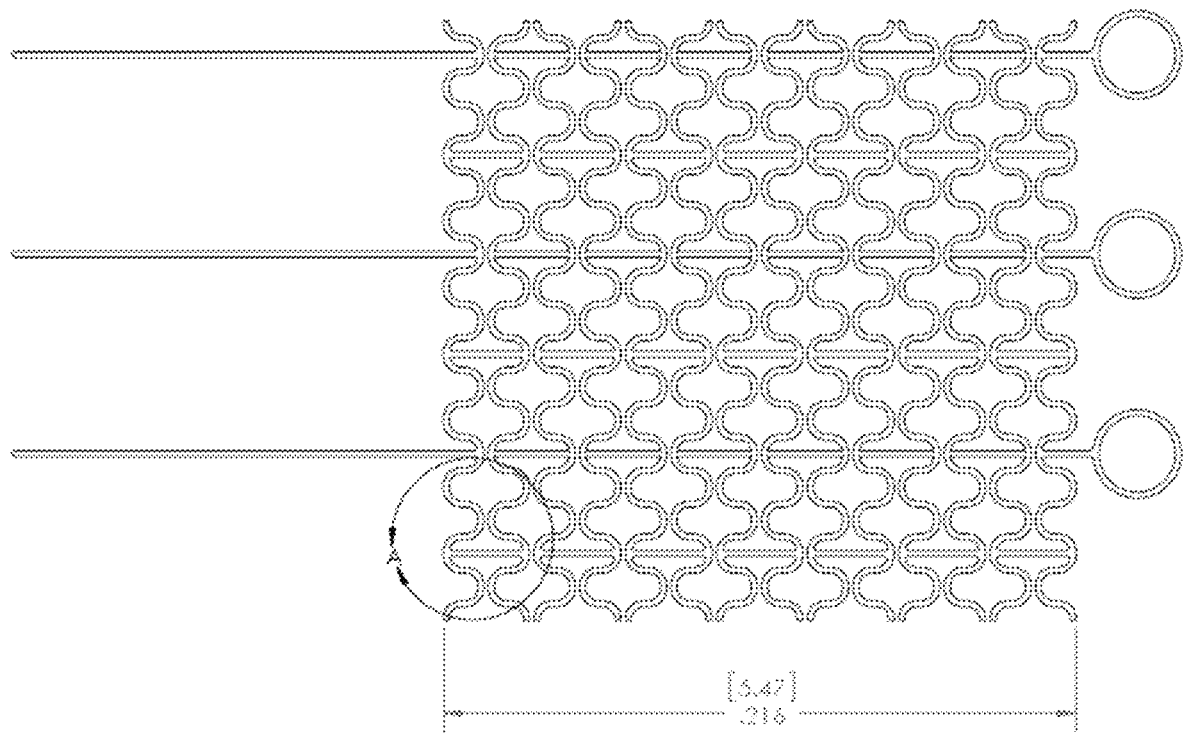
FIGS. 13A-13B show a plan views of a variation of a strut network having openings and struts that may form the tractor portion of a device (e.g., an atherectomy device) as described herein.
Figure 13B:
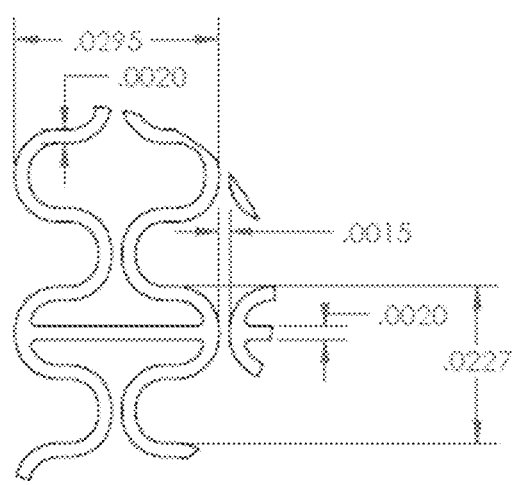
Figure 14A:
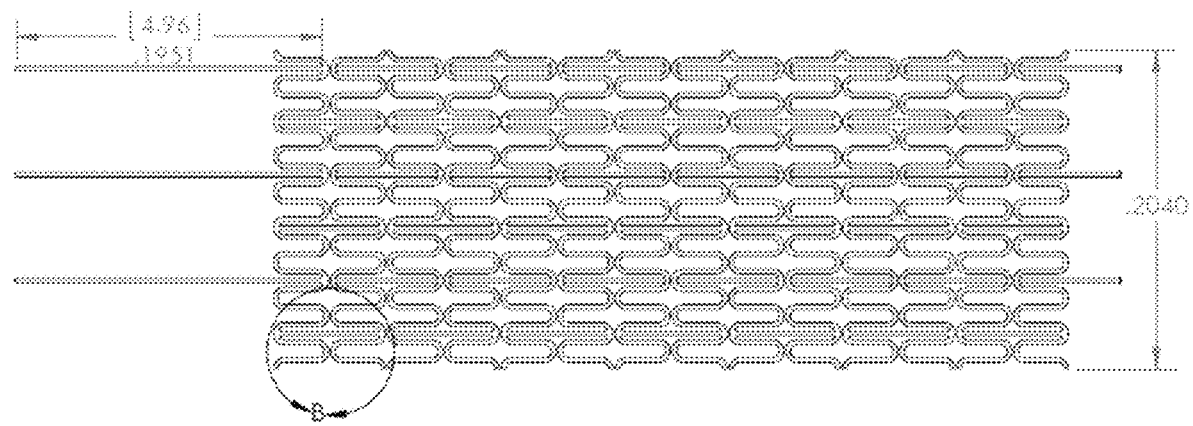
FIGS. 14A-14B show a plan views of a variation of a strut network having openings and struts that may form the tractor portion of a device (e.g., an atherectomy device) as described herein.
Figure 14B:
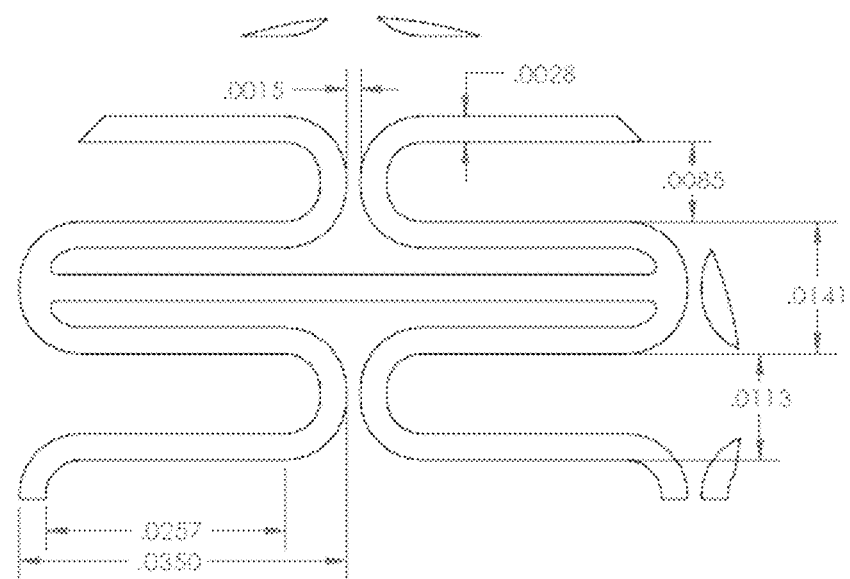
Figure 15A:
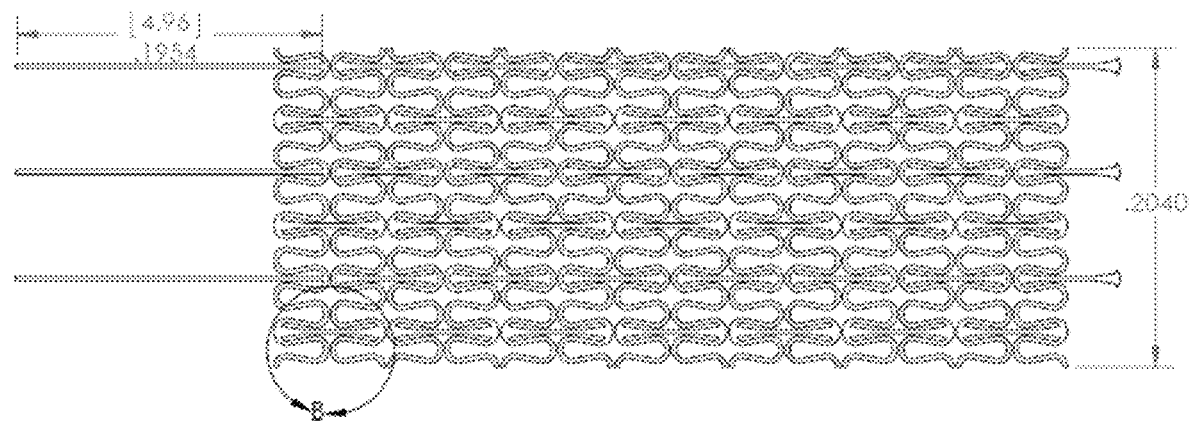
FIGS. 15A-15B show a plan views of a variation of a strut network having openings and struts that may form the tractor portion of a device (e.g., an atherectomy device) as described herein.
Figure 15B:
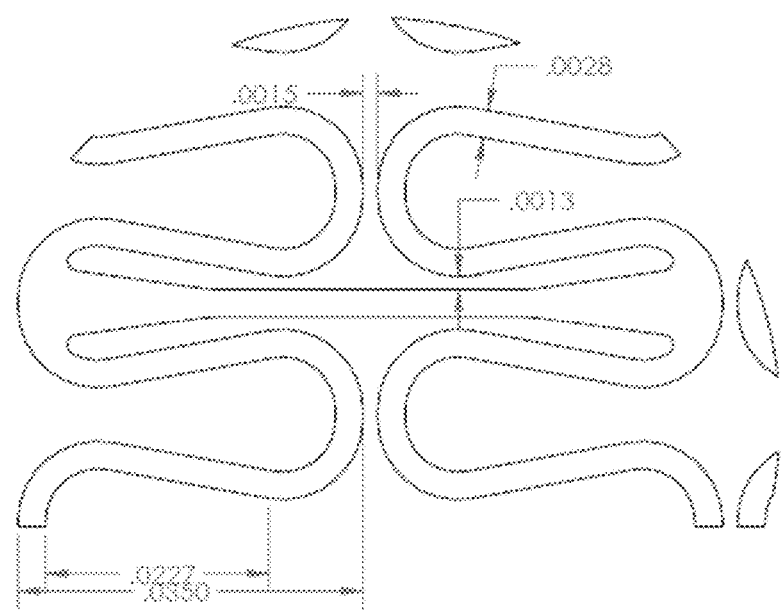
Figure 17A:
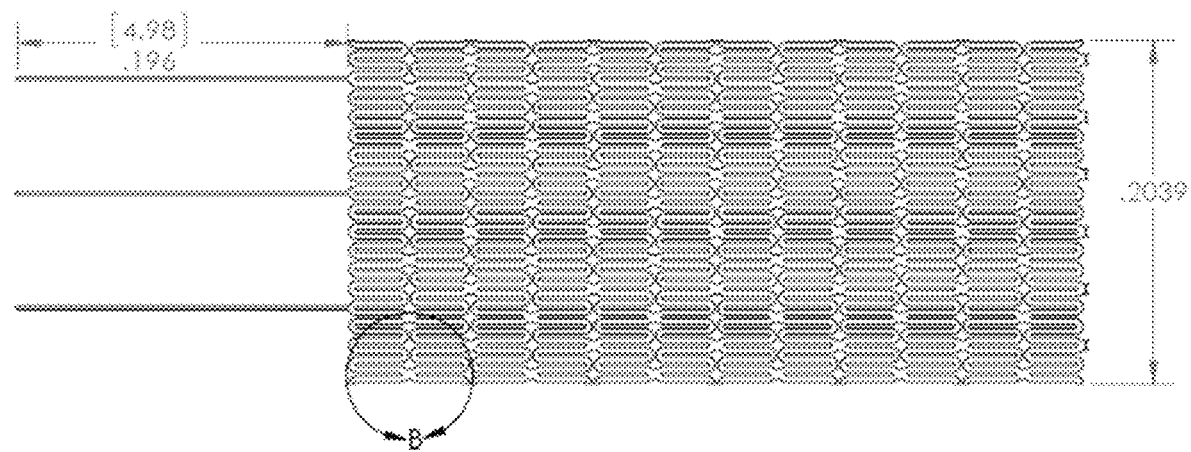
FIGS. 17A-17B show a plan views of a variation of a strut network having openings and struts that may form the tractor portion of a device (e.g., an atherectomy device) as described herein.
Figure 17B:
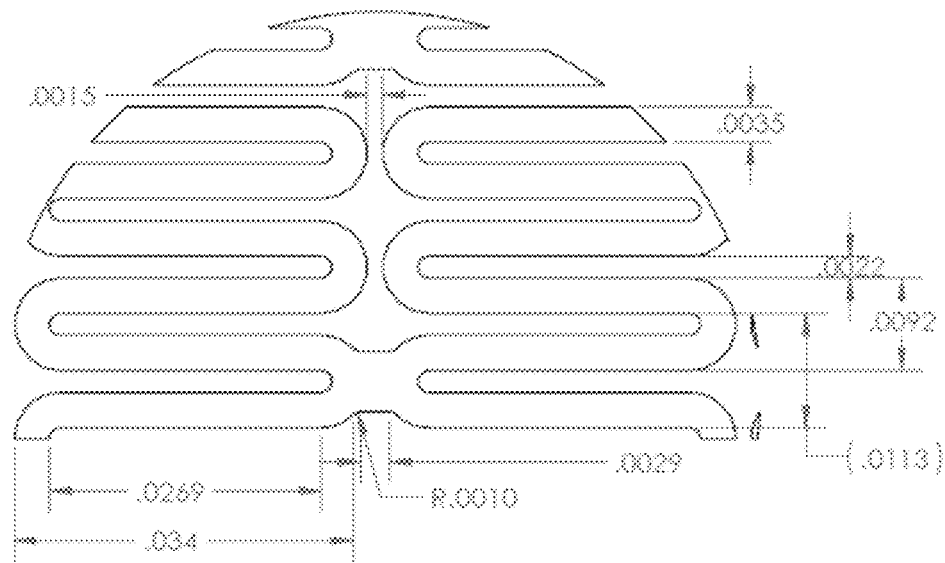
Figure 18A:
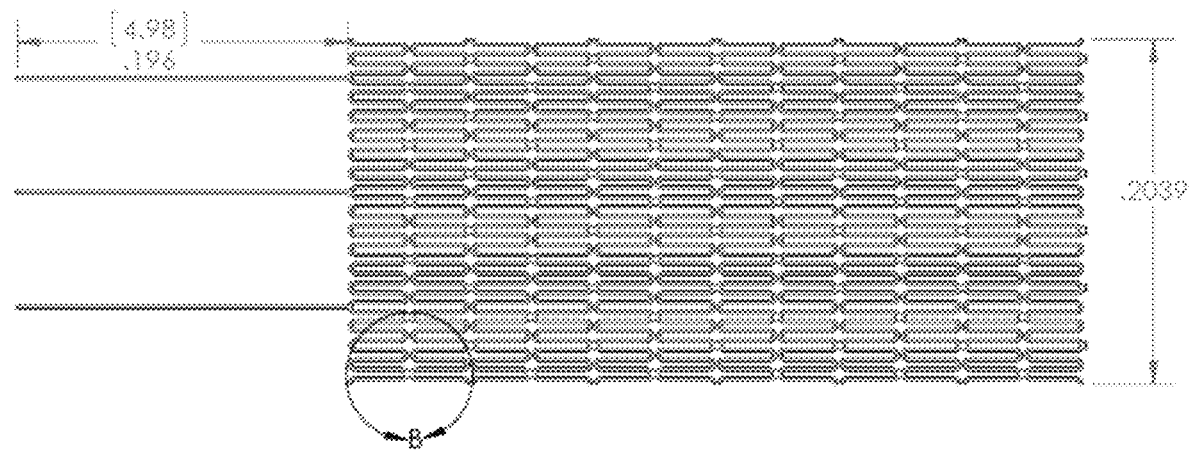
FIGS. 18A-18B show a plan views of a variation of a strut network having openings and struts that may form the tractor portion of a device (e.g., an atherectomy device) as described herein.
Figure 18B:
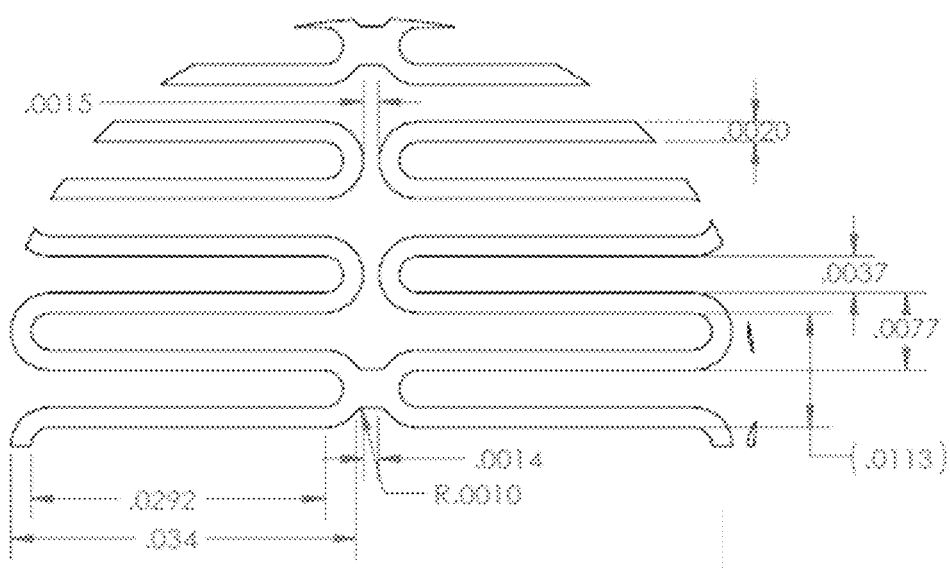
Figure 19A:
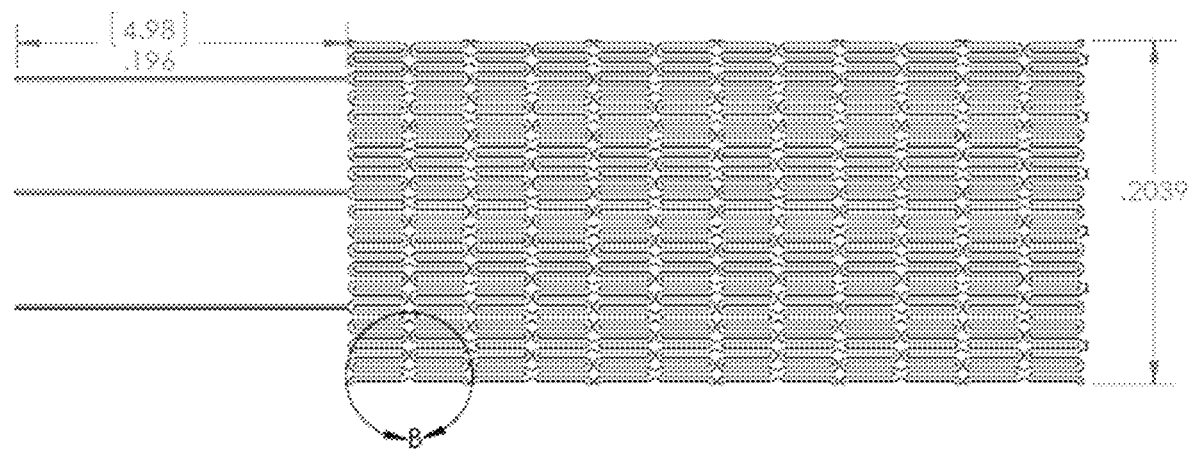
FIGS. 19A-19B show a plan views of a variation of a strut network having openings and struts that may form the tractor portion of a device (e.g., an atherectomy device) as described herein.
Figure 19B:
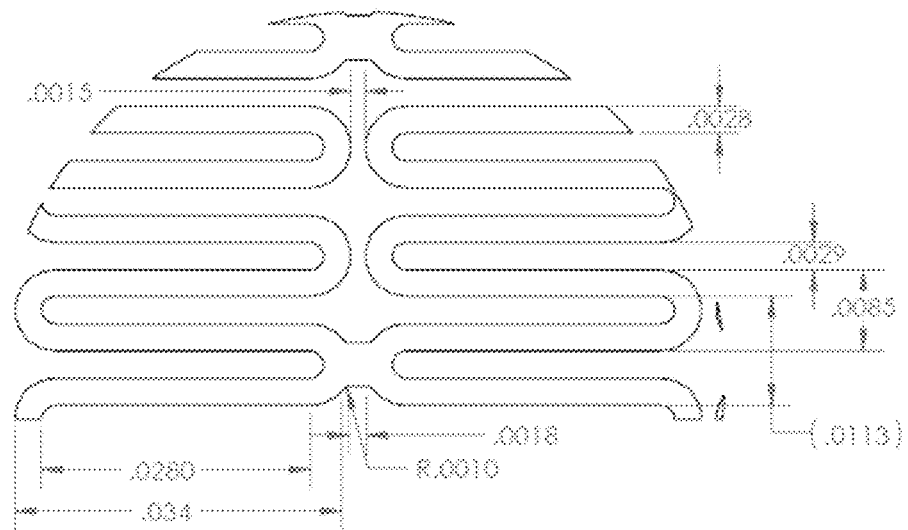
Figure 20A:
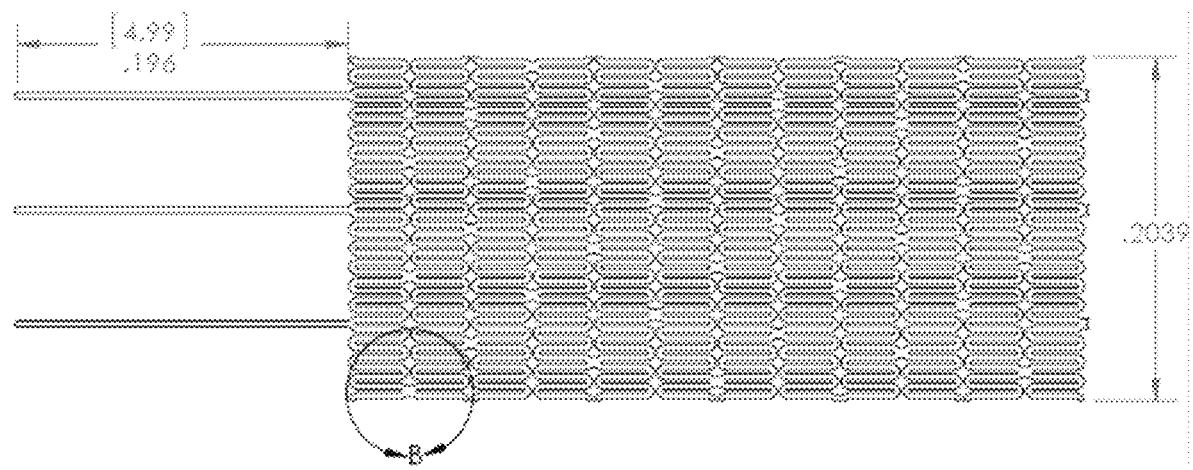
FIGS. 20A-20B show a plan views of a variation of a strut network having openings and struts that may form the tractor portion of a device (e.g., an atherectomy device) as described herein.
Figure 20B:
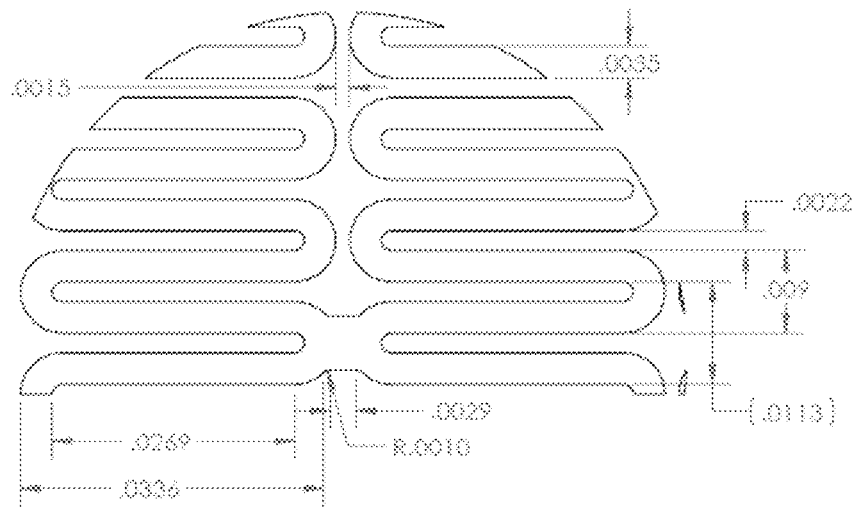
Figure 21A:
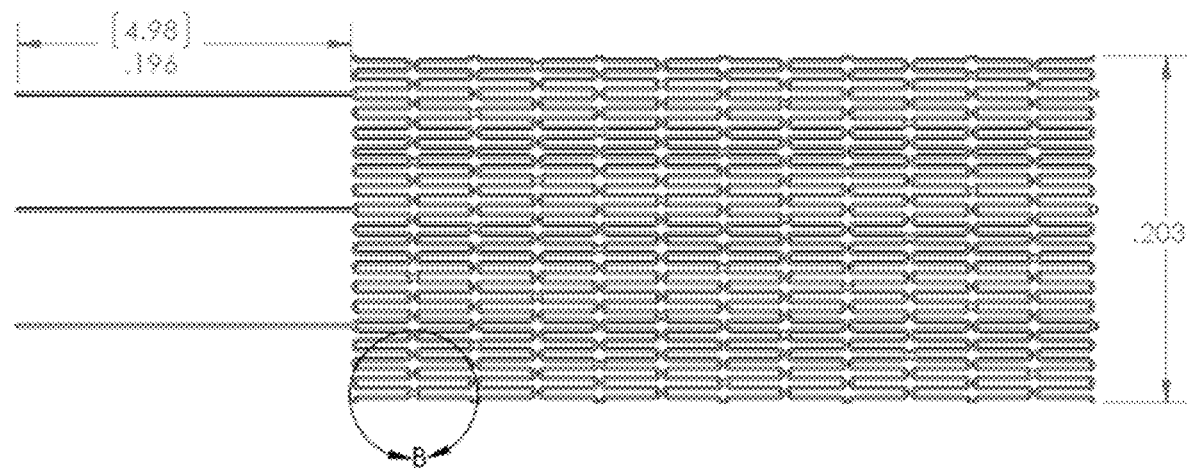
FIGS. 21A-21B show a plan views of a variation of a strut network having openings and struts that may form the tractor portion of a device (e.g., an atherectomy device) as described herein.
Figure 21B:
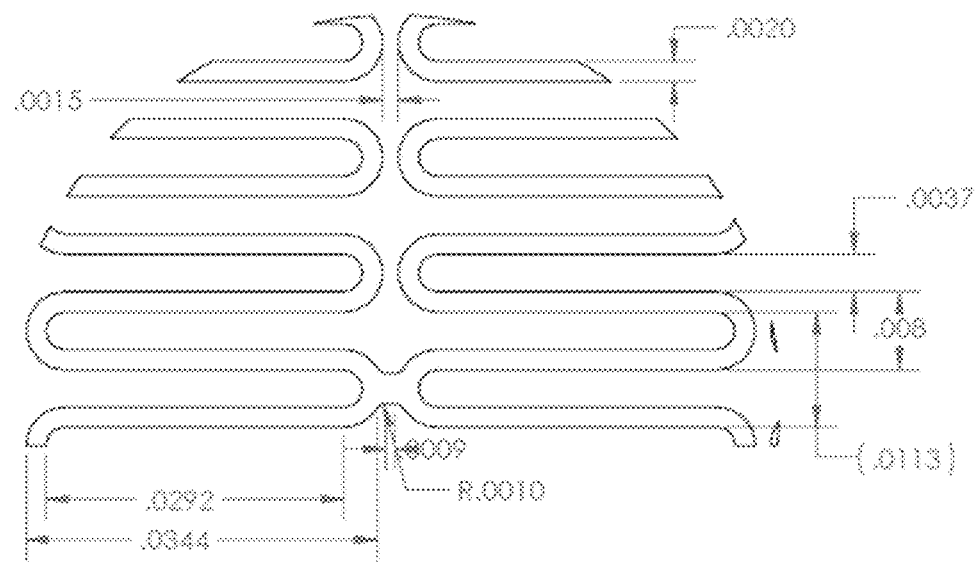
Figure 22A:
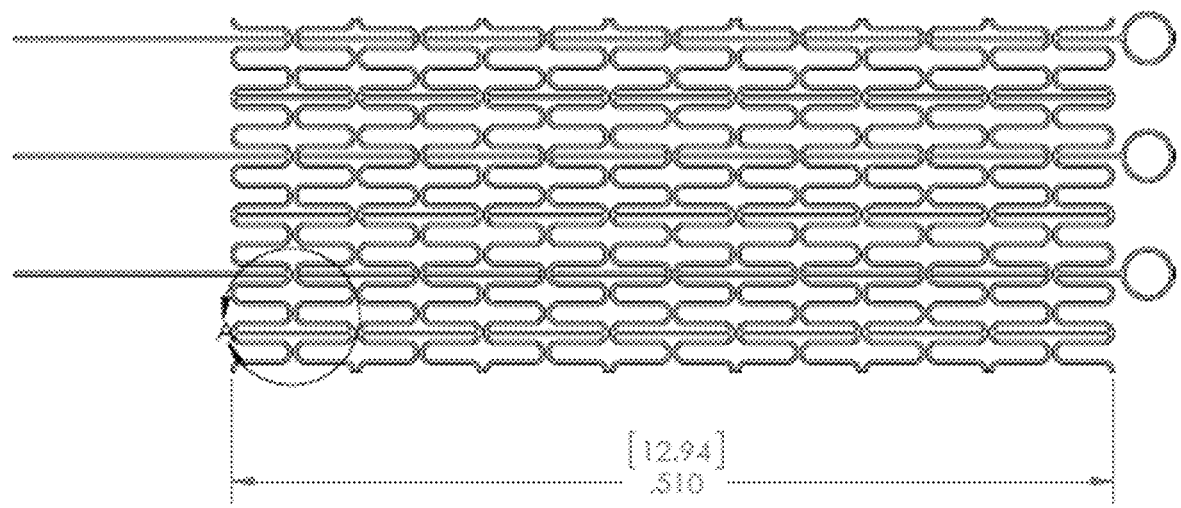
FIGS. 22A-22B show a plan views of a variation of a strut network having openings and struts that may form the tractor portion of a device (e.g., an atherectomy device) as described herein.
Figure 22B:
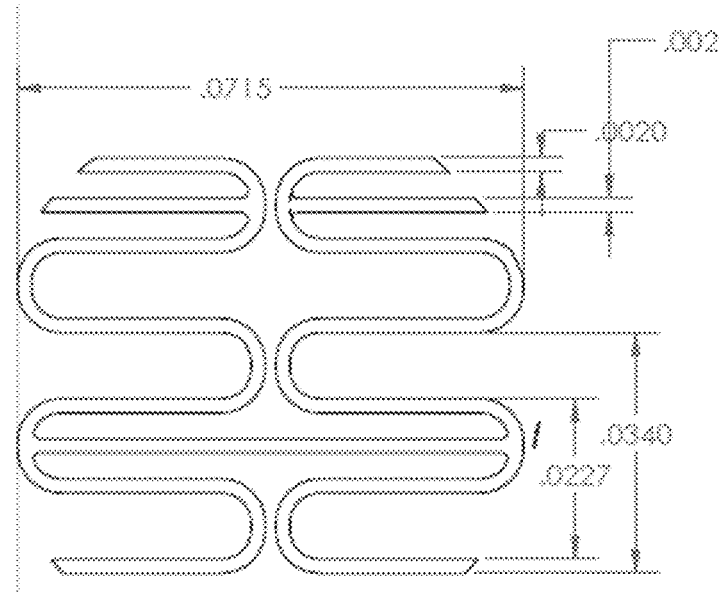
Figure 23A:
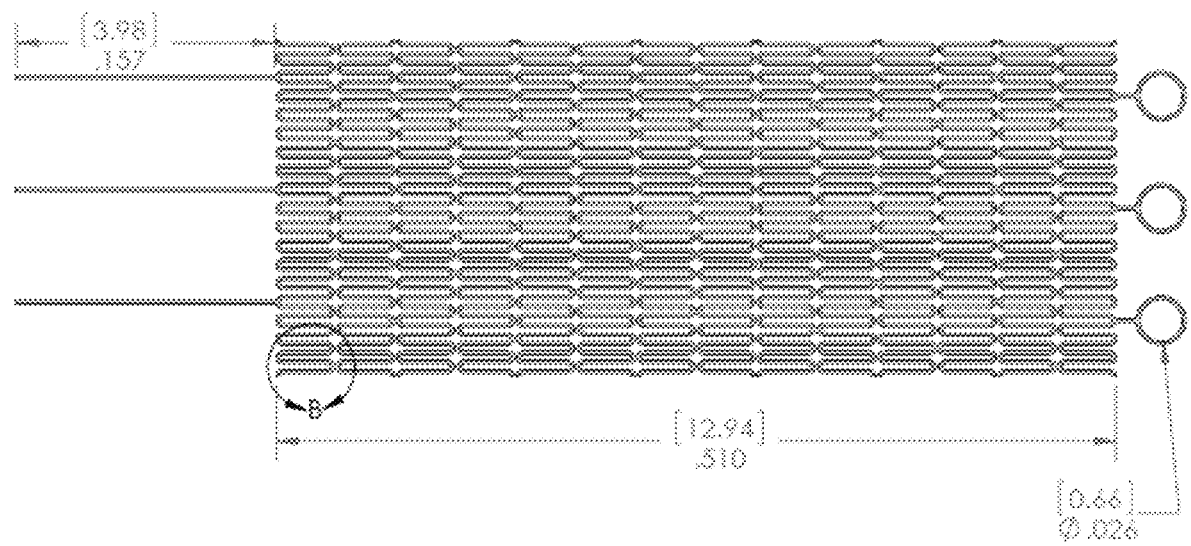
FIGS. 23A-23B show a plan views of a variation of a strut network having openings and struts that may form the tractor portion of a device (e.g., an atherectomy device) as described herein.
Figure 23B:
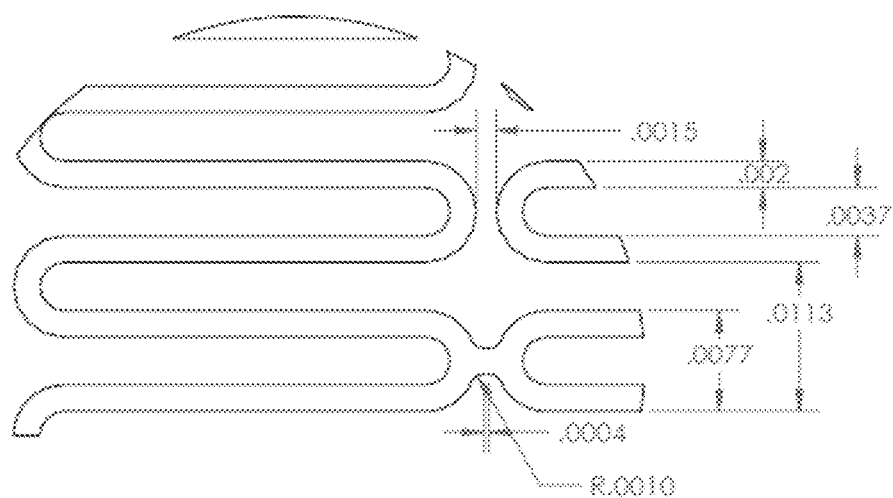
Figure 24A:
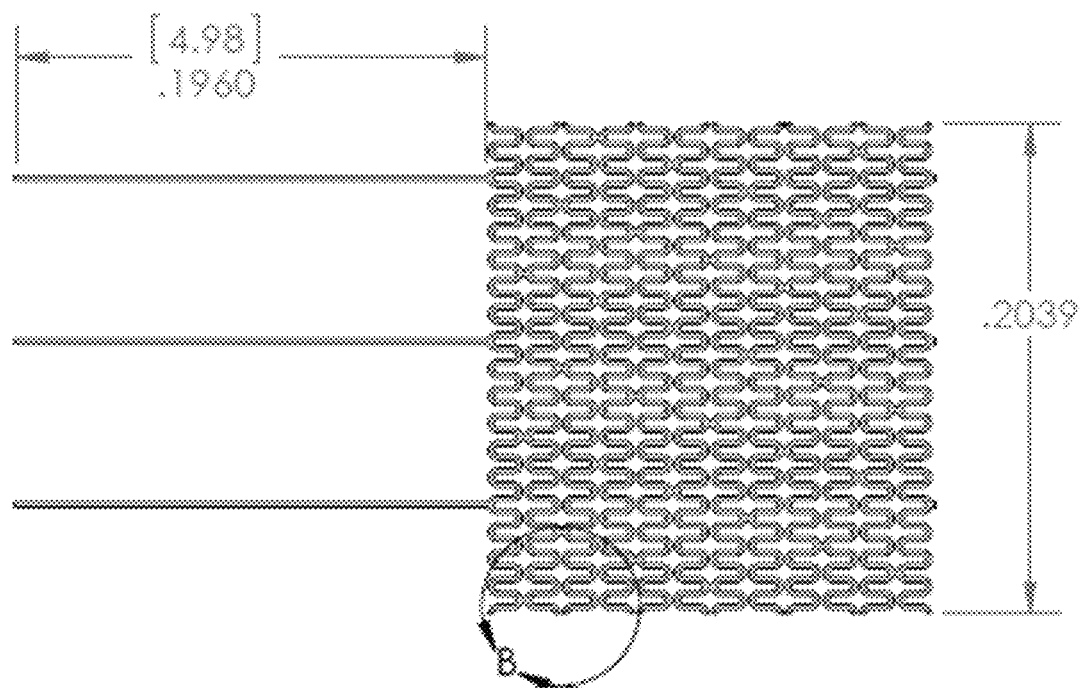
FIGS. 24A-24B show a plan views of a variation of a strut network having openings and struts that may form the tractor portion of a device (e.g., an atherectomy device) as described herein.
Figure 24B:
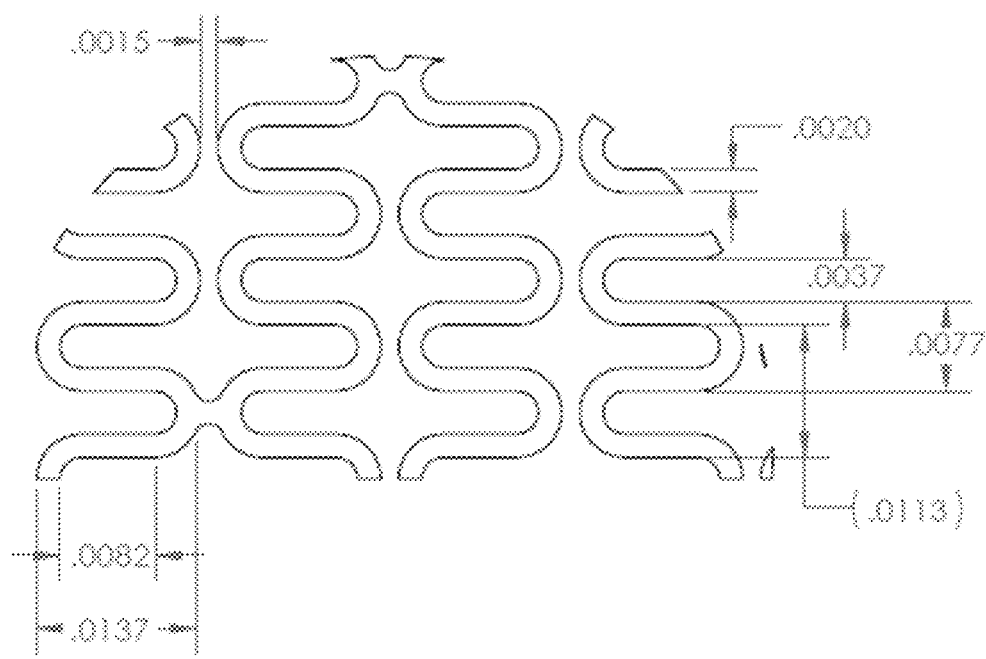
Figure 25:
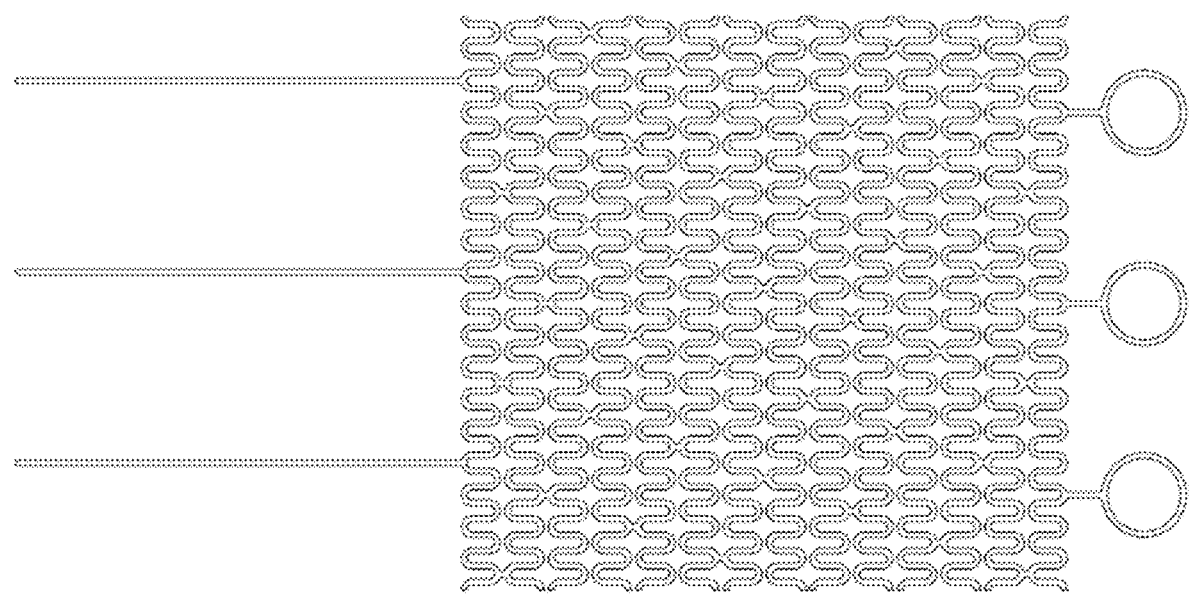
FIG. 25 shows a plan views of another variation of a strut network having openings and struts that may form the tractor portion of a device (e.g., an atherectomy device) as described herein.

FIG. 10 shows a plan view of a cutting pattern for a flexible tube with multiple openings 1044 and a network of struts 1043. FIGS. 11A-25 show plan views of various strut networks having openings and struts with different sizes and shapes. The struts can form a network of structures that perform various functions. For example, referring to FIG. 11A and inset view of FIG. 11B, the struts can form hoops 1108, hoop connectors 1110, engagement features 1106 and fastening elements 1116, 1116'. The openings 1151 and struts can have any shape. The shape of the openings 1151 and/or struts can at least partially dictate how the flexible tube moves, collapses, compresses, expands, etc. In some embodiments, the openings have shape corresponding to slits (kerfs), polygons (e.g., diamond, triangular, square, rectangular, pentagonal and/or hexagonal), circles, ovals, ellipses or irregular shapes. The shape and sizes of the struts corresponding to engagement features can at least partially dictate how the engagement features interact with the obstruction (e.g., scooping, gouging, cutting, etc.).

The sizes and shapes of the engagement features can be configured to engage with the obstruction in a prescribed manner, which may depend in part on characteristics of the obstruction. In some embodiments, an engagement feature has a shape in accordance with a gouger, poker, needle, dagger, lance, lancet, sickle, point or spear, which may provide a gouging action. In some embodiments, an engagement feature has a shape in accordance with a scooper, scraper, shovel, or spoon, which may provide a scooping or scraping action. In some embodiments, an engagement feature has a shape in accordance with a blade, cutter or knife, which may provide a cutting action (e.g., for breaking up obstructions). Engagement features that provide a combination of engagement actions (e.g., scooping, scraping, gouging and/or cutting) may be effective for capturing some obstructions.

According to some embodiments, the engagement features are formed by cutting a prescribed pattern of openings (e.g., holes and/or slits) within a sheet or tube. FIGS. 4A-4I show plan views of various cutting patterns for forming engagement features having different shapes and sizes, according to some embodiments. FIGS. 4A and 4C-4I show examples of various zig-zag cutting patterns for forming engagement features having sharp engagement surfaces. FIG. 4B shows an example of cutting patterns for forming engagement features having curved engagement surfaces. Sharper engagement surfaces may provide more of a gouging and/or cutting action, and curvier engagement features may provide more of a scooping or shoveling action. The sharpness of an engagement feature may be depend, in part, on an aspect ratio of a feature cut. Referring to FIG. 4D, for example, an aspect ratio of an engagement feature can refer to its width 475 divided by its height 477. Those engagement features having higher aspect ratios may provide more of a gouging action compared to engagement features having lower aspect ratios. FIG. 4C shows an example cutting pattern that provide an engagement feature having a first portion 471 having a first aspect ratio and a second portion 473 having a second aspect ratio different (e.g., greater) than the first aspect ratio.

In some cases, the tractor has engagement features with different shapes and sizes. For example, FIG. 4H shows a cutting pattern for forming hoop (row) of engagement features having a first type 481 and a second type 479, wherein the shapes (e.g., aspect ratios) of the first and second types of engagement features are different. A tractor and include any combination of engagement features having any of a number of different shapes and sizes. For example, a hoop can include any combination of sharp (e.g., FIGS. 4A and 4C-4I) and curved (e.g., FIG. 4B) engagement features. In some cases, a tractor includes a first hoop having a first type of engagement features (e.g., having a first shape and/or size) and a second hoop having a second type of engagement features (e.g., having a second shape and/or size). In some cases, a tractor includes a first hoop having a first combination of engagement features having different shapes and sizes, and a second hoop having a second combination of engagement features. In some embodiments, the engagement features include supplemental features 483, such as protruding barbs, holes, pores and/or nubs, which can facilitate engagement with the obstruction. FIG. 4I shows an example of engagement features having protruding barbs.

The laser cut path for cutting the various openings within the tube/sheet of material can be modified to affect the grabbing properties of the engagement features. FIGS. 5A and 5B show section views of laser cutting operations according to some embodiments. FIG. 5B shows a close-up view of FIG. 5A. The laser beam 508 may be directed at the tube/sheet 510 at a substantially perpendicular angle with respect to a surface of the tube/sheet. The resulting strut/engagement feature will have a substantially 90 degree cutting edge 512. FIGS. 6A and 6B show cross section views of a laser cutting operation according to another embodiment, where the laser beam 608 is directed at the tube/sheet 610 at a non-perpendicular angle 612, 612' (e.g., 5, 10, 20, 30, 40, 45, 50, 60, 70 80, 85, 95, 100, 110, 120, 130, 135, 140, 150, 160, 170 or 175 degrees) with respect to a surface of the tube/sheet. The resulting struts/engagement features will have correspondingly non-perpendicular edges. This process can be used to form engagement features having acute cutting edges, wherein the acute cutting edges have angles of less than 90 degrees (e.g., 5, 10, 20, 30, 40, 45, 50, 60, 70, 80, 85 or 89 degrees).

Figure 7:
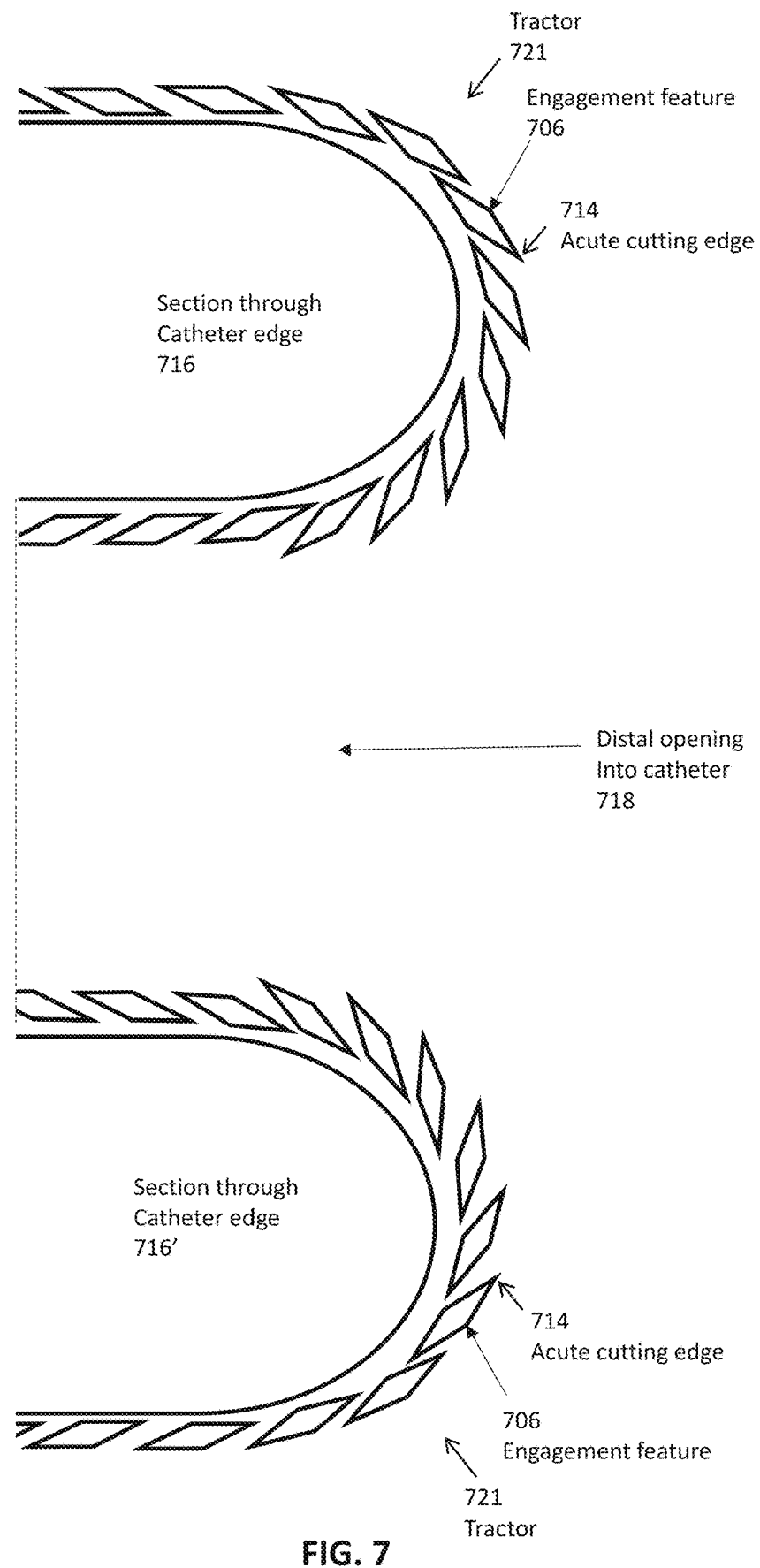
FIG. 7 shows a cross section view of a tractor having engagement features with acute cutting edges (not necessarily to scale).

FIG. 7 shows a cross sectional view of a tractor 721 having engagement features 706 with acute cutting edges 714 as it rotates (e.g., rolls) around an edge of a catheter (shown in cross-section 716, 716' at the distal end opening 718). When the flexible tube is installed on the catheter, the acute cutting edges can be aligned along the longitudinal axis of the catheter. When the tractor is activated, the acute angle cutting edges can interact with the obstruction differently than a perpendicular cutting edge. The acute angle cutting edge may result in sharper engagement features and more effective grabbing surfaces than perpendicular cutting edges. In some cases, the acute angle cutting edge provides more of a scraping action that is more effective for scraping a surface of the obstruction compared to a perpendicular cutting edge. In some cases, the acute angle cutting edge provides more of a gouging action that is more effective for gouging the obstruction compared to a perpendicular cutting edge. In some cases, the acute angle cutting edge provides a higher grabbing strength to the tractor compared to a perpendicular cutting edge.

According to some embodiments, a laser cutting technique is used to form very small kerfs or slits with the tube/sheet. For example, a laser beam can be used to form kerfs/slits having widths of 0.001 inches or less (e.g., 0.0009, 0.0008, 0.0005 or 0.0001 inches). The opening between feature (e.g., engagement features) of the tube/sheet can be spaced accordingly. Forming very small kerfs/slits instead of larger openings may allow for formation of the various features (e.g., engagement features) of the tractor without substantial damage to surfaces of the tractor. Furthermore, forming very small kerfs/slits increase the efficiency of forming the tractor. Additionally, forming very small kerfs/slits may result in substantially no removal of material, which can result in cost savings of the manufacturing process.

Figure 8A:
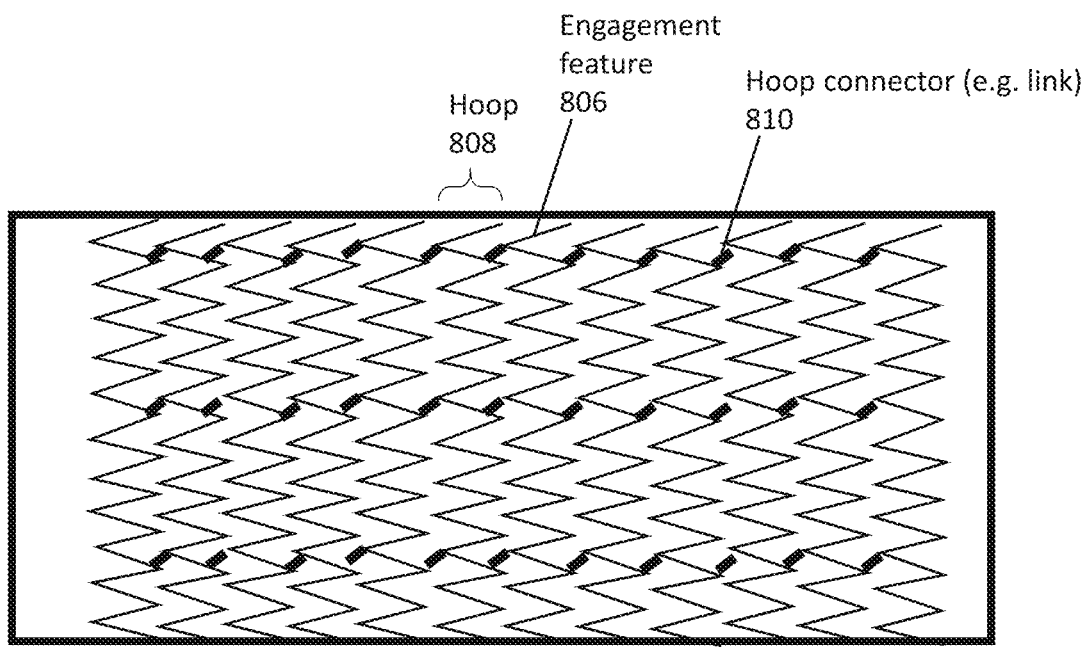
FIGS. 8A and 8B show plan views of unrolled tractors having different connector arrangements.
Figure 8B:
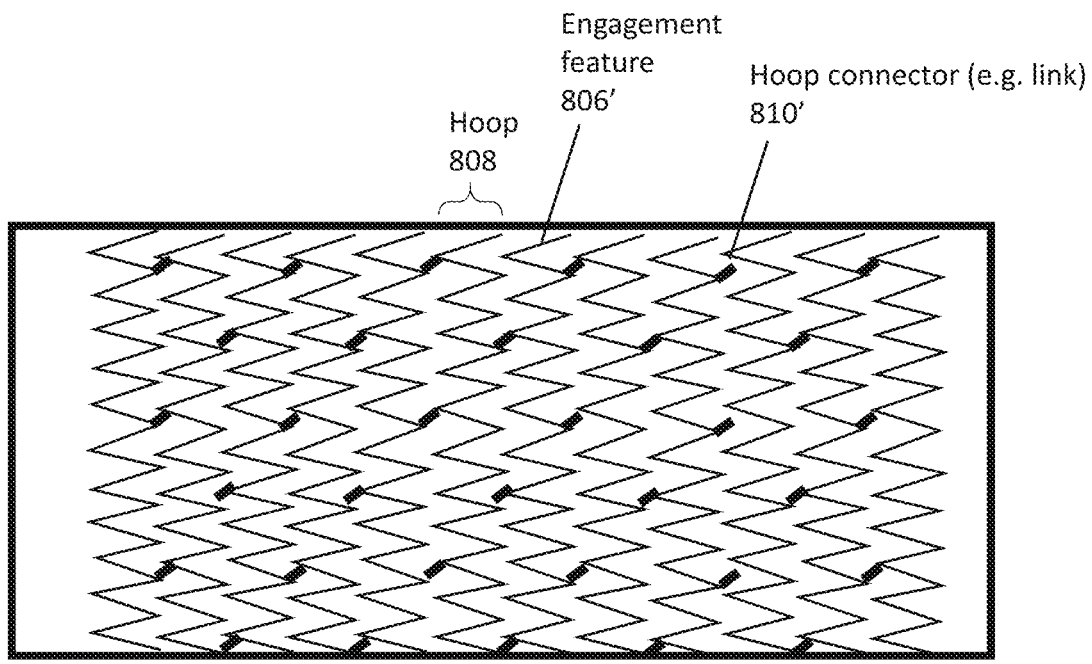

In some cases, the arrangement of the hoop connectors is configured to provide a prescribed flexibility to the tractor during operation. FIGS. 8A and 8B show plan views of unrolled tractors having two different hoop connector 810, 810' arrangements. As used herein a hoop 808 may refer to a row of engagement members 806, 806'. In some variations the 'row' of engagement members (engagement features) is a single continuous row that spirals around the flexible tube body. In FIG. 8A, the links (e.g., hoop connectors) line up in phase (three per hoop/circumference) with three engagement features between each hoop connector of a given hoop. In FIG. 8B, there are three hoop connectors per hoop/circumference and three engagement features between each hoop connector of a given hoop (similar to FIG. 8A), but the hoop connectors are out of phase with respect to each other. That is, at least some of the hoop connectors of adjacent hoops do not line up along the same plane. The flexibility (e.g., collapsibility) of the tractors of FIGS. 8A and 8B may differ such that the pulling force required to roll the tractor around the catheter edge will differ. In some applications, the required pulling force is minimized.

In some applications, the grabbing device may be used in combination with one or more other devices for removing the obstruction. Returning to FIG. 3A, for example, the engagement features may project beyond the catheter edge as it rolls over the catheter edge. As the engagement features project outward, they may "score/etch/texture" the obstruction in a way that make stress concentration lines within the blockage. These stress concentration lines may improve the post blockage removal flow dynamics (boundary layer) using, for example, an angioplasty balloon for further vessel dilation. For example, the texture/scoring may help highly calcified plaques crack open with less balloon pressure and create more uniform vessel expansion. The extent to which the engagement features project from the catheter edge can correspond to the extent of scoring on the blockage. One way of controlling the extent to which the engagement features project from the catheter edge is to control the size (e.g., height) and/or stiffness (malleability) of material the engagement features.

The catheter may have design features such as column strength, torque transmission, ability to travel over a guide wire, ability to reach distant treatment sites in small vessels through highly curvy (tortuous vessel). According to some embodiments, the tractor is configured to allow the catheter to move and be guided within a blood vessel with little to no hindrance from presence of the tractor. For instance, the tractor can be configured to allow the catheter to bend and twist normally so as to negotiate a small bend radius (tight curve). Properties of the tractor can be chosen to prevent or minimize impediment of the motion of the catheter while being guided through the blood vessel. For example, a smaller tractor wall thickness may increase the maneuverability of the catheter compared to a thicker tractor wall thickness. A tractor having a smaller profile can add very little thickness to the grabbing device compared to the thickness of the catheter alone. In particular, a thin tractor may only minimally increase the outer and inner diameters of the grabbing device compared to the catheter alone. This can allow the grabbing device to maneuver within the blood vessel while minimizing damage to the blood vessel and surrounding tissues. Furthermore, the access hole used to introduce the grabbing device into the patient would be minimized. That is, catheter-based technologies using smaller outer diameter catheters (e.g., French size) can translate into less invasive procedures.

Figure 9:
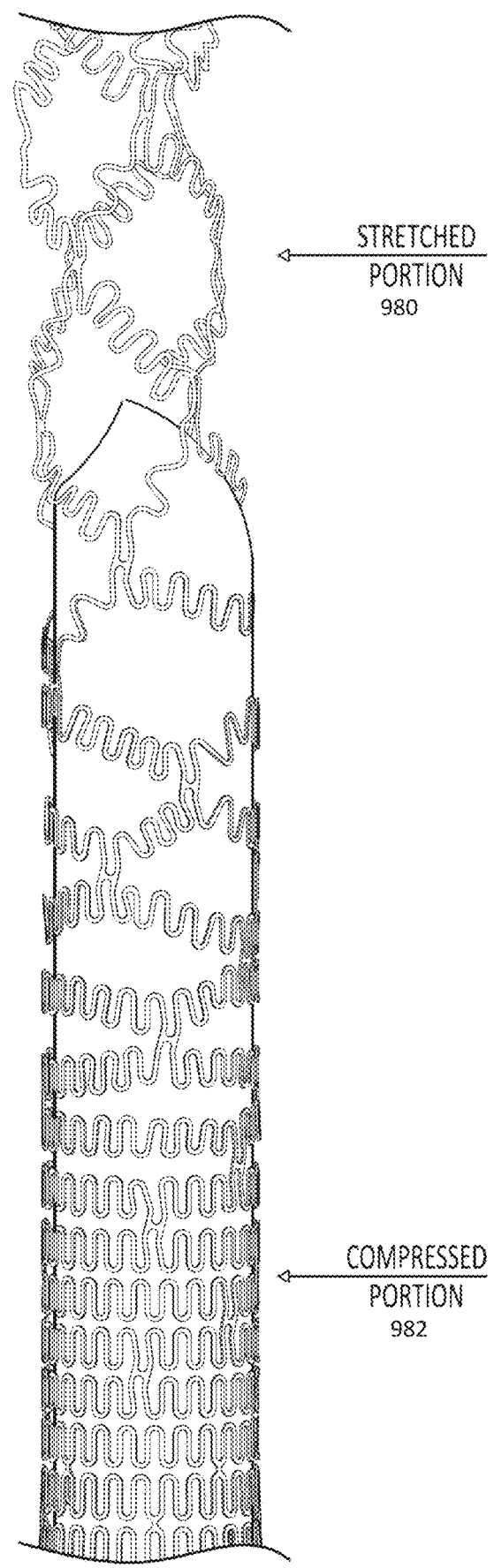
FIG. 9 shows a perspective view of a tractor that includes a stretched portion.

The material of the tractor may affect the operation of the grabbing device. For example, a tractor made of a more ductile material may be able to bend and change shape when exposed to forces during operation. For example, the pulling force placed on the tractor may stretch the network of struts such that some of the hoops, engagement features and/or hoop connectors become elongated along the longitudinal axis of the catheter. In some cases, engagement with the obstruction may cause a change in shape of the engagement features. In some applications, it is preferable to have a more ductile tractor. For example, it may be desirable to have portions of the tractor to transition from a compressed form to a more elongated (stretched) for during operation. FIG. 9 shows a perspective view of a tractor that includes stretched 980 and compressed 982 portions, where the ductile properties of the material of the tractor causes some of the hoops to become elongated when a pulling force is applied. This may allow the tractor to deform to a smaller diameter when in the elongated state, thereby facilitating the entry of the tractor within the internal cavity of the catheter. In some application, it is preferable to have a stiffer tractor. For example, it may be desirable for the tractor to rigidly maintain its dimensions during operation. In some embodiments, tractors made of steel or alloys of steel are more ductile than tractors made of harder alloys such as nickel titanium.

The tractor can be configured to interact with the catheter in a prescribed manner. In some embodiments, the flexible tube of the tractor has an inner diameter that is equal to or slightly smaller (undersized) than the outer diameter of the catheter prior to installation onto the catheter, such that the tractor closely hugs the catheter surface when installed. An undersized flexible tube may provide the most communication between the tractor and the catheter, such that the tractor is stabilized by the catheter and remain in relatively fixed position in relation to the catheter until a sufficiently high pulling force is applied. In some cases, the tractor can having an inner diameter of 0.001 inches greater than the outer diameter of the catheter or less (e.g., 0.0009, 0.0008, 0.0007, 0.0006 or 0.0005 inches greater) may provide a hand-in-glove fit. In some embodiments, the flexible tube of the tractor is sufficiently larger than the outer diameter of the catheter such that friction between the tractor and the catheter is minimal, thereby reducing the force (rolling force) needed to roll the tractor over the catheter edge. In some cases, the tractor can having an inner diameter of more than 0.001 inches greater than the outer diameter of the catheter (e.g., 0.0011, 0.002, 0.003, 0.005, 0.01 or 0.1 inches greater) may provide a tractor with a minimal required rolling force. In some embodiments, a first portion of the flexible tube has an inner diameter of 0.001 inches greater than the outer diameter of the catheter or less, and a second portion of the flexible tube has an inner diameter of more than 0.001 inches greater than the outer diameter of the catheter. Such combinations of various tractor inner diameters may provide optimal stability with minimal required rolling force in certain applications.

In some embodiments, different portions of the flexible tube can be in various compressed and expanded states. The compressed and expanded states can be associated with different amounts of stored energy. Examples of different compressed and expanded states are described in U.S. Patent Application Publication No. 2018/0070968 A1, which is incorporated by reference herein in its entirety. A flexible tube (or portions of the flexible tube) in compressed and expanded states can have different outer and/or inner diameters. For example, the inner diameter of the flexible tube (or a portion thereof) in an expanded state may be 1.5 times greater than the outer diameter of the catheter or greater (e.g., 1.6, 1.7, 1.8, 1.9, 2.0, 2.5, 3.0 or 4.0 times greater). In such cases, the expanded diameter may increase the grabbing capacity of the grabbing device. In some embodiments, the grabbing capacity may increase by at least four times the volume for each double in expansion of the outer diameter of the flexible tube relative to the outer diameter of the catheter. In some applications, the outer diameter of the flexible tube (or portions thereof) is configured to expand when released from a compressed state. In such cases, the grabbing device may be constrained by a delivery sheath to maintain an outer diameter of the flexible tube until use (expansion).

In some cases, the flexible tube includes one or more markers that can be used to identify a position of the grabbing device within the blood vessel. In some instances, the marker(s) is made of a radio-opaque material, which can be detectable using radio transmission imaging. The marker(s) may be part of the network of struts and hoops, or may be a separate member that is added to the flexible tube. In some embodiments, the marker is a band as part of the grabbing device. In some cases, the marker(s) is located near a proximal end of the flexible tube within the internal cavity of the catheter. Examples of markers are described in U.S. Patent Application Publication No. 2018/0070968 A1 and U.S. Pat. No. 10,028,759 B2, each of which is incorporated by reference herein in its entirety.

Table 1 summarizes how some of properties of a grabbing device may affect various functions of the grabbing device.

TABLE 1

| | | Effect on Grabbing Device | | | | |
|---|---|---|---|---|---|---|
| Property | Rolling force | Grabbing Strength Dense Obstruction | Grabbing Strength Soft Obstruction | Catheter tracking (pre-roll) | Stability/ Durability on outside of catheter (pre-roll) | Radio-opacity |
| Material | | | | | | |
| Steel (304) | higher | increase | No effect | good | best | increase |
| Nickel Titanium | lower | decrease | No effect | better | good | decrease |
| Wall thickness | | | | | | |
| thicker | increase | increase | decrease | worse | increase | increase |
| thinner | decrease | decrease | increase | better | decrease | decrease |
| Number of hoops/cm length | | | | | | |
| increase | No effect | decrease | increase | better | increase | No effect |
| decrease | No effect | increase | decrease | worse | decrease | No effect |
| Number of Waves/cm | | | | | | |
| increase | decrease | decrease | increase | No effect | No effect | No effect |
| decrease | increase | increase | decrease | No effect | No effect | No |

TABLE 1-continued

| | | | | | Stability/ | |
| | | Grabbing | Grabbing | | Durability on | |
| | | Strength | Strength | Catheter | outside of | |
| | Rolling | Dense | Soft | tracking | catheter (pre- | Radio- |
| Property | force | Obstruction | Obstruction | (pre-roll) | roll) | opacity |
|---|---|---|---|---|---|---|
| | | | | | | effect |
| *Number of Connections per perimeter* | | | | | | |
| increase | No effect | decrease | increase | decrease | increase | No effect |
| decrease | No effect | increase | decrease | increase | decrease | No effect |
| Hoop Connection alignment | Minimal effect | decrease | Minimal | decrease | No effect | No effect |
| *Engagement Feature Height* | | | | | | |
| taller | No effect | Significant Increase | increase | decrease | No effect | No effect |
| Engagement Feature tip shape (pointy) | No effect | increase | No effect | No effect | Minimal effect | No effect |
| Engagement Feature width (wider) | Increase | minimal | increase | No effect | Minimal effect | increase |
| Proximal markers (bigger) | No effect | No effect | No effect | No effect | No effect | increase |
| Off axis laser cut (non-perpendicular) | No effect | No effect | No effect | No effect | No effect | No effect |

Regarding the type of material, Table 1 indicates that in some cases a tractor (flexible tube) made of a relatively ductile material (SAE 304 stainless steel) can provide a grabbing device having a higher grabbing strength for a dense obstruction, higher stability/durability, and higher radio-opacity compared to a tractor made of a less ductile material (nickel titanium alloy). Table 1 indicates that in some cases a tractor made of a relatively rigid material (nickel titanium alloy) can provide a grabbing device having a lower required rolling force and improved catheter tracking (ability to allow catheter to move freely) compared to a tractor made of a less rigid material (SAE 304 stainless steel). Table 1 indicates that in some cases the tractor material has substantially no effect on the grabbing strength for soft obstructions of the grabbing device.

Regarding the wall thickness of the tractor, Table 1 indicates that in some cases a tractor (flexible tube) having a relatively thick wall thickness can provide a grabbing device having a higher grabbing strength for a dense obstruction, higher stability/durability, and higher radio-opacity compared to a tractor having a relatively thin wall thickness. Table 1 indicates that in some cases a tractor having a relatively thin wall thickness can provide a grabbing device having a lower required rolling force, higher grabbing strength for a soft obstruction, and improved catheter tracking compared to a tractor having a relatively thin wall thickness.

Regarding the density of hoops, Table 1 indicates that in some cases a tractor having a higher hoop density (greater number of hoops per centimeter length) can provide a grabbing device having a higher grabbing strength for soft obstructions, improved catheter tracking, and higher stability/durability compared to a tractor having a lower hoop density. Table 1 indicates that in some cases a tractor having a lower hoop density (lower number of hoops per centimeter length) can provide a grabbing device having a higher grabbing strength for dense obstructions compared to a tractor having a greater hoop density. Table 1 indicates that in some cases the hoop density has substantially no effect on the rolling force, and radio-opacity of the grabbing device.

Regarding the density of engagement features, Table 1 indicates that in some cases a tractor having a higher engagement feature density (greater number of engagement features per centimeter) can provide a grabbing device having a lower required rolling force and a higher grabbing strength for soft obstructions compared to a tractor having a lower engagement feature density. Table 1 indicates that in some cases a tractor having a lower engagement feature density (lower number of engagement features per centimeter) can provide a grabbing device having a higher grabbing strength for dense obstructions compared to a tractor having a higher engagement feature density. Table 1 indicates that in some cases the density of engagement features has substantially no effect on the catheter tracking, stability/durability and the radio-opacity of the grabbing device.

Regarding the density of hoop connectors, Table 1 indicates that in some cases a tractor having a higher hoop connector density (greater number of hoop connectors along a perimeter of the tractor) can provide a grabbing device having a lower required rolling force and a higher grabbing strength for soft obstructions and higher stability/durability compared to a tractor having a lower hoop connector density. Table 1 indicates that in some cases a tractor having a lower hoop connector density (lower number of hoop connectors along a perimeter of the tractor) can provide a grabbing device having a higher grabbing strength for dense obstructions and improved catheter tracking compared to a tractor having a hoop connector density. Table 1 indicates that in some cases the density of hoop connectors has substantially no effect on the rolling force and the radio-opacity of the grabbing device.

Regarding the arrangement of hoop connectors, Table 1 indicates that in some cases a tractor having more hoop connectors that are aligned (as opposed to offset from each other) can decrease the grabbing strength of dense obstructions and decrease the catheter tracking compared to a tractor having less hoop connectors that are aligned. Table 1 indicates that in some cases a tractor having more or less hoop connectors that are aligned has minimal effect on the rolling force of the tractor and on the grabbing strength of soft obstructions of the grabbing device. Table 1 indicates that in some cases a tractor having more or less hoop connectors that are aligned has substantially no effect on the stability/durability and radio-opacity of the grabbing device.

Regarding the height of engagement features, Table 1 indicates that in some cases a tractor having engagement features with greater heights (taller) can significantly increase the grabbing strength of dense obstructions and increase the grabbing strength of soft obstructions compared to a tractor having lesser heights. Table 1 indicates that in some cases the height of the engagement feature of a tractor has substantially no effect on the rolling force, the stability/durability and the radio-opacity of the grabbing device.

Regarding the shape of the engagement features, Table 1 indicates that in some cases a tractor having more pointed engagement features (e.g., sharper) can significantly increase the grabbing strength of dense obstructions and minimally effects the stability/durability of the grabbing device. Table 1 indicates that in some cases the pointedness (sharpness) of the engagement feature of a tractor has substantially no effect on the rolling force, grabbing strength of soft obstructions, catheter tracking and radio-opacity of the grabbing device.

Regarding proximal markers, Table 1 indicates that in some cases a tractor having a radio-opaque marker at or near the proximal end of the flexible tube has substantially no effect on the on the rolling force, grabbing strength of dense or soft obstructions, catheter tracking and stability/durability of the grabbing device.

Regarding the cross sectional angle of the cutting edges of engagement features, Table 1 indicates that in some cases a tractor having engagement features with a greater number of acute cutting edges (e.g., less than 90 degrees) can have substantially no effect on the rolling force, grabbing strength of dense or soft obstructions, catheter tracking, stability/durability and radio-opacity of the grabbing device.

According to some embodiments, a grabbing device effective for capturing an obstruction from a blood vessel has a tractor with 3 to 5 engagement features per centimeter (cm) length, 2 to 3 hoops per centimeter length, and 0.5 engagement features per millimeter (mm) per hoop perimeter.

Example 1

A grabbing device was made according to the following specification:

| | |
|---|---|
| Material | SAE 304 stainless steel |
| Tractor wall thickness | 0.001 inches |
| Tractor outer diameter | 1.64 mm (0.64 inches) |
| Tractor inner diameter | 1.6 mm (0.62 inches) |
| Engagement feature heights | 3 mm |
| Engagement feature widths | 0.0015 inches |
| Hoop density | 3 hoops per cm |
| Engagement feature density | 18 engagement features per hoop perimeter |
| Hoop connector arrangement | Repeated arrangement of Hoops 1 and 2, where: Hoop 1: 3 connectors equally spaced (5 engagement features between each hoop connector Hoop 2: 3 connectors shifted by 3 engagement features with respect to Hoop 1; 18 engagement features per perimeter |

Example 2

A grabbing device was made according to the following specification:

| | |
|---|---|
| Material | Nickel titanium alloy |
| Tractor wall thickness | 0.001 inches |
| Tractor outer diameter | 1.64 mm (0.64 inches) |
| Tractor inner diameter | 1.6 mm (0.62 inches) |
| Engagement feature heights | 3 mm |
| Engagement feature widths | 0.002 inches |
| Hoop density | 3 hoops per cm |
| Engagement feature density | 18 engagement features per hoop perimeter |
| Hoop connector arrangement | Repeated arrangement of Hoops 1 and 2, where: Hoop 1: 3 connectors equally spaced (5 engagement features between each hoop connector Hoop 2: 3 connectors shifted by 3 engagement features with respect to Hoop 1; 18 engagement features per perimeter |

Example 3

A grabbing device was made according to the following specification:

| | |
|---|---|
| Material | SAE 304 stainless steel |
| Tractor wall thickness | 0.00075 inches |
| Tractor outer diameter | 1.64 mm (0.64 inches) |
| Tractor inner diameter | 1.6 mm (0.625 inches) |
| Engagement feature heights | 3 mm |
| Engagement feature widths | 0.002 inches |
| Hoop density | 3 hoops per cm |
| Engagement feature density | 18 engagement features per hoop perimeter |
| Hoop connector arrangement | Repeated arrangement of Hoops 1 and 2, where: Hoop 1: 3 connectors equally spaced (5 engagement features between each hoop connector Hoop 2: 3 connectors shifted by 3 engagement features with respect to Hoop 1; 18 engagement features per perimeter |

Any of the methods (including those associated with user interfaces) described herein may be implemented as software, hardware or firmware, and may be described as a non-transitory computer-readable storage medium storing a set of instructions capable of being executed by a processor (e.g., of a computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, the foregoing description is provided primarily for exemplary purposes and should not be interpreted to limit the scope of the invention as it is set forth in the claims.

What is claimed is:

1. An atherectomy device for removing a plaque material from a blood vessel, the device comprising:
   a catheter having a distal edge defining an opening that provides access to a lumen within the catheter; and
   a tractor comprising a flexible tube that at least partially covers and extends along an outer surface of the catheter and inverts over the catheter distal edge, such that a first end of the flexible tube extends through the opening into the lumen of the catheter,
   wherein the flexible tube comprises a plurality of engagement features cut at an acute angle into an outer surface of the flexible tube and through the flexible tube to form a plurality of acute cutting edges oriented towards the distal edge, and
   wherein the flexible tube is configured so that pulling the first end of the flexible tube proximally through the catheter lumen causes the flexible tube to roll and invert over the catheter distal edge, thereby exposing the acute cutting edges distally as the flexible tube rolls into the catheter lumen.

2. The device of claim 1, wherein the acute cutting edges are aligned along a length of the flexible tube.

3. The device of claim 1, wherein the acute cutting edges are configured scrape the plaque material on a wall of the blood vessel when the first end of the flexible tube is pulled proximally through the catheter lumen.

4. The device of claim 1, wherein the acute cutting edges are configured to gouge the plaque material on a wall of the blood vessel when the first end of the flexible tube is pulled proximally through the catheter lumen.

5. The device of claim 1, wherein the plurality of engagement features are arranged into a series of circumferential bands extending along a length of the flexible tube, such that the respective bands of engagement features pass sequentially over the distal edge of the catheter as the flexible tube rolls into the catheter lumen.

6. The device of claim 5, further comprising a series of links, wherein each link of the series extends between respective adjacent bands of engagement features.

7. The device of claim 6, wherein the links are arranged in a circumferentially offset pattern along the length of the flexible tube.

8. The device of claim 6, wherein the links are arranged in a circumferentially aligned pattern along the length of the flexible tube.

9. The device of claim 1, wherein the engagement features comprise a first set of features defined by having a first aspect ratio, and a second set of features defined by having a second aspect ratio that is different than the first aspect ratio.

10. The device of claim 1, wherein the engagement features comprise a first set of features defined by having sharp engagement surfaces, and a second set of features defined by having curved engagement surfaces.

11. The device of claim 1, wherein engagement features of a first set of the engagement features have a first shape configured for shoveling the plaque material, and engagement features of a second set of the engagement features have a second shape configured for gouging the plaque material.

12. The device of claim 1, wherein engagement features of a first set of the engagement features have a first shape configured for cutting the plaque material, and engagement features of a second set of the engagement features have a second shape configured for gouging the plaque material.

13. The device of claim 1, wherein engagement features of a first set of the engagement features have a first shape configured for cutting the plaque material, engagement features of a second set of the engagement features have a second shape configured for gouging the plaque material, and engagement features of a third set of the engagement features have a third shape configured for shoveling the plaque material.

14. An atherectomy device for removing a plaque material from a blood vessel, the device comprising:
   a catheter having distal end portion configured for entering the blood vessel, and a distal edge that defines an opening that provides access to an internal lumen of the catheter; and
   an activatable tractor comprising a flexible tube that at least partially covers and extends along an outer surface of the distal end portion of the catheter and inverts over the catheter distal edge, such that an end portion of the flexible tube extends through the opening into the internal lumen of the catheter, the flexible tube having an outer surface comprising a series of spaced-apart circumferential bands of engagement features having a plurality of different shapes and configured to engage with the plaque material, wherein the engagement features of at least to adjacent bands are circumferentially offset from one another,
   wherein when the tractor is activated, the flexible tube moves around the catheter distal edge such that the engagement features protrude from the distal edge to engage with and direct the plaque material toward the internal lumen.

15. The device of claim 14, wherein the engagement features comprise a first set of protruding features defined by having a first aspect ratio and a second set of protruding features defined by having a second aspect ratio different than the first aspect ratio.

16. The device of claim 14, wherein the engagement features comprise a first set of protruding features defined by having sharp engagement surfaces and a second set of protruding features defined by having curved engagement surfaces.

17. The device of claim 14, wherein engagement features of a first set of the engagement features have a first shape configured for shoveling the plaque material, and engagement features of a second set of the engagement features have a second shape configured for gouging the plaque material.

18. The device of claim 14, wherein a first set of the engagement features has a first shape configured for cutting the plaque material, and a second set of the engagement features has a second shape configured for gouging the plaque material.

19. The device of claim 14, wherein engagement features of a first set of the engagement features has a first shape configured for cutting the plaque material, engagement features of a second set of the engagement features has a second shape configured for gouging the plaque material, and engagement features of a third set of the engagement features has a third shape configured for shoveling the plaque material.

20. The device of claim 14, wherein when the tractor is activated, the flexible tube moves around the catheter distal edge in a reciprocating motion.

21. An atherectomy device for removing a plaque material from a blood vessel, comprising:
- a catheter having a distal edge that defines an opening that provides access to an internal lumen; and
- a tractor comprising a flexible tube that covers at least a portion of the distal edge and enters the internal lumen of the catheter, the flexible tube comprising a series of bands with engagement features that are configured to engage with the plaque material, wherein at least a portion of the bands have an offset arrangement where the engagement features of adjacent bands are offset from one another,
- wherein when the tractor is activated, each of the bands passes over the distal edge such that the engagement features protrude from the distal edge to engage with and direct the plaque material toward the internal lumen.

22. The device of claim 21, wherein each band has three to five engagement features per centimeter length of the band.

23. The device of claim 21, wherein the flexible tube has two to three bands per centimeter length of the flexible tube.

24. The device of claim 21, wherein the flexible tube comprises a plurality of band connectors that connect the series of bands.

25. The device of claim 21, wherein the band connectors are in an offset arrangement with respect to each other within the flexible tube.

26. The device of claim 21, wherein the band connectors are in an aligned arrangement with respect to each other within the flexible tube.

27. The device of claim 21, wherein a second portion of the bands have an aligned arrangement where the engagement features of adjacent bands are aligned with one another.

28. The device of claim 21, wherein the flexible tube comprises a plurality of fastening elements that couple the flexible tube to a puller that provides a pulling force.

* * * * *